(12) United States Patent
Eggers et al.

(10) Patent No.: US 7,505,812 B1
(45) Date of Patent: Mar. 17, 2009

(54) ELECTROSURGICAL SYSTEM FOR TREATING RESTENOSIS OF BODY LUMENS

(75) Inventors: Philip E. Eggers, Dublin, OH (US);
Hira V. Thapliyal, Los Altos, CA (US)

(73) Assignee: ArthroCare Corporation, Austin, TX (US)

( * ) Notice: Subject to any disclaimer, the term of this patent is extended or adjusted under 35 U.S.C. 154(b) by 0 days.

(21) Appl. No.: 09/354,835

(22) Filed: Jul. 16, 1999

Related U.S. Application Data

(62) Division of application No. 08/874,173, filed on Jun. 13, 1997, now Pat. No. 6,179,824.

(51) Int. Cl.
*A61N 1/30* (2006.01)
(52) U.S. Cl. .................................................... 604/20
(58) Field of Classification Search ............ 606/39, 606/41, 46, 32; 607/99, 105, 113; 604/35, 604/114, 22
See application file for complete search history.

(56) References Cited

U.S. PATENT DOCUMENTS

| | | | |
|---|---|---|---|
| 2,050,904 A | 8/1936 | Trice | 219/31 |
| 2,056,377 A | 10/1936 | Wappler | |
| 3,460,539 A | 8/1969 | Anhalt | 128/304 |
| 3,633,425 A | 1/1972 | Sanford | 73/356 |
| 3,769,984 A | 11/1973 | Muench | 128/404 |
| 3,815,604 A | 6/1974 | OMalley et al. | |
| 3,828,780 A | 8/1974 | Morrison, Jr. et al. | |
| 3,901,242 A | 8/1975 | Storz | |
| 3,920,021 A | 11/1975 | Hiltebrandt | |
| 3,939,839 A | 2/1976 | Curtiss | |
| 3,970,088 A | 7/1976 | Morrison | |
| 4,011,872 A | 3/1977 | Komiya | 606/47 |
| 4,033,351 A | 7/1977 | Hetzel | |
| 4,038,519 A | 7/1977 | Foucras | 392/472 |
| 4,040,426 A | 8/1977 | Morrison, Jr. | |
| 4,043,342 A | 8/1977 | Morrison, Jr. | |
| 4,060,087 A | 11/1977 | Hiltebrandt | |
| 4,074,718 A | 2/1978 | Morrison, Jr. | |
| 4,092,986 A | 6/1978 | Schneiderman | |

(Continued)

FOREIGN PATENT DOCUMENTS

CA     2067412     9/2004

(Continued)

OTHER PUBLICATIONS

V.E. Elsasser et al. *Acta Medicotechnicá* vol. 24, No. 4, pp. 129-134 (1976).

(Continued)

*Primary Examiner*—Manuel A Mendez
(74) *Attorney, Agent, or Firm*—Brian E. Szymczak; Matthew Scheele

(57) ABSTRACT

The present invention comprises apparatus and methods for maintaining patency in body passages subject to occlusion by invasive tissue growth. The apparatus and methods of the present invention may be used to open and maintain patency in virtually any hollow body passage which may be subject to occlusion by invasive cellular growth or invasive solid tumor growth. Suitable hollow body passages include ducts, orifices, lumens, and the like, with exemplary body passages including the coronary arteries. The present invention is particularly useful for reducing or eliminating the effects of restenosis in coronary arteries by selectively removing tissue ingrowth in or around stents anchored therein.

20 Claims, 12 Drawing Sheets

U.S. PATENT DOCUMENTS

| | | |
|---|---|---|
| 4,116,198 A | 9/1978 | Roos |
| 4,181,131 A | 1/1980 | Ogiu |
| 4,184,492 A | 1/1980 | Meinke et al. |
| 4,202,337 A | 5/1980 | Hren et al. |
| 4,228,800 A | 10/1980 | Degler, Jr. et al. |
| 4,232,676 A | 11/1980 | Herczog |
| 4,248,231 A | 2/1981 | Herczog et al. |
| 4,326,529 A | 4/1982 | Doss et al. |
| 4,381,007 A | 4/1983 | Doss |
| 4,474,179 A | 10/1984 | Koch .......................... 606/40 |
| 4,476,862 A | 10/1984 | Pao |
| 4,532,924 A | 8/1985 | Auth et al. |
| 4,548,207 A | 10/1985 | Reimels |
| 4,567,890 A | 2/1986 | Ohta et al. |
| 4,582,056 A | 4/1986 | McCorkle, Jr. |
| 4,582,057 A | 4/1986 | Auth |
| 4,590,934 A | 5/1986 | Malis et al. |
| 4,593,691 A | 6/1986 | Lindstrom et al. |
| 4,641,649 A | 2/1987 | Walinsky |
| 4,643,186 A | 2/1987 | Rosen |
| 4,646,737 A | 3/1987 | Hussein |
| 4,654,024 A | 3/1987 | Crittenden |
| 4,658,817 A | 4/1987 | Hardy |
| 4,660,571 A | 4/1987 | Hess et al. |
| 4,672,962 A | 6/1987 | Hershenson |
| 4,674,499 A | 6/1987 | Pao |
| 4,682,596 A * | 7/1987 | Bales et al. ................... 606/39 |
| 4,699,157 A | 10/1987 | Shonk ........................ 607/122 |
| 4,706,667 A | 11/1987 | Roos |
| 4,709,698 A | 12/1987 | Johnston et al. |
| 4,727,874 A | 3/1988 | Bowers et al. |
| 4,753,223 A | 6/1988 | Bremer ....................... 600/140 |
| 4,754,752 A | 7/1988 | Ginsburg et al. .............. 606/27 |
| 4,765,331 A | 8/1988 | Petruzzi et al. |
| 4,785,806 A | 11/1988 | Deckelbaum |
| 4,785,815 A | 11/1988 | Cohen |
| 4,785,823 A | 11/1988 | Eggers et al. |
| 4,796,622 A | 1/1989 | Lu et al. ...................... 606/28 |
| 4,799,479 A | 1/1989 | Spears |
| 4,805,616 A | 2/1989 | Pao |
| 4,823,791 A | 4/1989 | D'Amelio et al. |
| 4,832,048 A | 5/1989 | Cohen |
| 4,857,046 A | 8/1989 | Stevens et al. ................ 604/22 |
| 4,860,743 A | 8/1989 | Abela |
| 4,860,752 A | 8/1989 | Turner |
| 4,907,586 A | 3/1990 | Bille et al. |
| 4,907,589 A | 3/1990 | Cosman ....................... 606/34 |
| 4,920,978 A | 5/1990 | Colvin |
| 4,931,047 A | 6/1990 | Broadwin et al. |
| 4,936,281 A | 6/1990 | Stasz |
| 4,936,301 A | 6/1990 | Rexroth et al. |
| 4,943,290 A | 7/1990 | Rexroth et al. |
| 4,955,377 A | 9/1990 | Lennox et al. |
| 4,966,597 A | 10/1990 | Cosman |
| 4,967,765 A | 11/1990 | Turner et al. |
| 4,968,314 A | 11/1990 | Michaels |
| 4,976,709 A | 12/1990 | Sand |
| 4,976,711 A | 12/1990 | Parins et al. |
| 4,979,948 A | 12/1990 | Geddes et al. |
| 4,998,933 A * | 3/1991 | Eggers et al. ................. 606/41 |
| 5,000,751 A | 3/1991 | Schroder et al. .............. 606/4 |
| 5,007,908 A | 4/1991 | Rydell |
| 5,009,656 A | 4/1991 | Reimels |
| 5,035,696 A | 7/1991 | Rydell |
| 5,041,109 A | 8/1991 | Abela |
| 5,047,026 A | 9/1991 | Rydell |
| 5,047,027 A | 9/1991 | Rydell |
| 5,057,105 A | 10/1991 | Malone et al. |
| 5,057,106 A | 10/1991 | Kasevich et al. |
| 5,078,684 A | 1/1992 | Yasuda ....................... 604/95 |
| 5,078,717 A | 1/1992 | Parins et al. |
| 5,078,736 A | 1/1992 | Behl |
| 5,080,660 A | 1/1992 | Buelna |
| 5,083,535 A | 1/1992 | Deschler et al. .......... 123/192.2 |
| 5,083,565 A | 1/1992 | Parins |
| 5,084,044 A | 1/1992 | Quint |
| 5,085,659 A | 2/1992 | Rydell |
| 5,088,997 A | 2/1992 | Delahuerga et al. |
| 5,093,877 A | 3/1992 | Aita |
| 5,098,431 A | 3/1992 | Rydell |
| 5,099,840 A | 3/1992 | Goble |
| 5,102,410 A | 4/1992 | Dressel |
| 5,104,391 A | 4/1992 | Ingle et al. .................... 606/71 |
| 5,108,391 A | 4/1992 | Flachenecker et al. |
| RE33,925 E | 5/1992 | Bales |
| 5,112,330 A | 5/1992 | Nishigaki et al. |
| 5,114,402 A | 5/1992 | McCoy .................... 604/95.05 |
| 5,122,138 A * | 6/1992 | Manwaring ................. 606/46 |
| 5,125,924 A | 6/1992 | Rudko |
| 5,125,926 A | 6/1992 | Rudko |
| 5,125,928 A | 6/1992 | Parins et al. |
| 5,137,530 A | 8/1992 | Sand |
| 5,140,987 A | 8/1992 | Schuger et al. |
| 5,152,759 A | 10/1992 | Parel et al. |
| 5,156,151 A | 10/1992 | Imran |
| 5,163,938 A | 11/1992 | Kambara et al. .............. 606/47 |
| 5,167,659 A | 12/1992 | Ohtomo et al. |
| 5,171,311 A | 12/1992 | Rydell et al. |
| 5,178,618 A | 1/1993 | Kandarpa |
| 5,178,620 A | 1/1993 | Eggers et al. |
| 5,188,635 A | 2/1993 | Radtke |
| 5,190,517 A | 3/1993 | Zieve et al. |
| 5,190,540 A | 3/1993 | Lee |
| 5,192,280 A | 3/1993 | Parins |
| 5,195,959 A | 3/1993 | Smith |
| 5,196,006 A | 3/1993 | Klopotek |
| 5,197,466 A | 3/1993 | Marchosky et al. |
| 5,197,963 A | 3/1993 | Parins |
| 5,200,604 A | 4/1993 | Rudko |
| 5,201,757 A | 4/1993 | Heyn et al. .................. 606/198 |
| 5,207,675 A | 5/1993 | Canady |
| 5,217,455 A | 6/1993 | Tan |
| 5,217,457 A | 6/1993 | Delahuerga et al. |
| 5,217,459 A | 6/1993 | Kamerling |
| 5,222,938 A | 6/1993 | Behl |
| 5,224,953 A | 7/1993 | Morgentaler |
| 5,230,334 A | 7/1993 | Klopotek |
| 5,234,457 A | 8/1993 | Andersen ................... 606/198 |
| 5,242,386 A | 9/1993 | Holzer |
| 5,242,399 A | 9/1993 | Lau et al. .................... 604/104 |
| 5,242,441 A | 9/1993 | Avitall ........................ 606/41 |
| 5,246,438 A | 9/1993 | Langberg |
| 5,250,045 A | 10/1993 | Bohley |
| 5,261,410 A | 11/1993 | Alfano |
| 5,263,951 A | 11/1993 | Spears et al. |
| 5,267,994 A | 12/1993 | Gentelia et al. |
| 5,267,997 A | 12/1993 | Farin et al. |
| 5,273,524 A | 12/1993 | Fox et al. |
| 5,277,201 A | 1/1994 | Stern |
| 5,279,299 A | 1/1994 | Imran |
| 5,281,211 A | 1/1994 | Parel et al. |
| 5,281,216 A | 1/1994 | Klicek |
| 5,281,218 A | 1/1994 | Imran |
| 5,282,797 A | 2/1994 | Chess |
| 5,282,824 A | 2/1994 | Gianturco ................. 623/1.13 |
| 5,287,861 A | 2/1994 | Wilk ......................... 128/898 |
| 5,290,273 A | 3/1994 | Tan |
| 5,290,282 A | 3/1994 | Casscells |
| 5,292,321 A | 3/1994 | Lee |
| 5,293,868 A | 3/1994 | Nardella |
| 5,300,069 A | 4/1994 | Hunsberger et al. |
| 5,304,170 A | 4/1994 | Green |
| 5,306,238 A | 4/1994 | Fleenor |
| 5,312,395 A | 5/1994 | Tan |

| | | | | | |
|---|---|---|---|---|---|
| 5,312,400 A | 5/1994 | Bales et al. | 5,556,397 A | 9/1996 | Long et al. |
| 5,314,406 A | 5/1994 | Arias et al. | 5,569,242 A | 10/1996 | Lax et al. |
| 5,318,525 A | 6/1994 | West | 5,571,100 A | 11/1996 | Goble et al. |
| 5,324,254 A | 6/1994 | Phillips | 5,571,169 A | 11/1996 | Plaia et al. |
| 5,330,470 A | 7/1994 | Hagen | 5,579,764 A | 12/1996 | Goldreyer |
| 5,330,496 A | 7/1994 | Alferness | 5,584,872 A | 12/1996 | LaFontaine et al. |
| 5,334,140 A | 8/1994 | Phillips | 5,591,159 A | 1/1997 | Taheri |
| 5,334,190 A | 8/1994 | Seiler | 5,603,731 A | 2/1997 | Whitney |
| 5,334,193 A | 8/1994 | Nardella ................ 606/41 | 5,607,421 A | 3/1997 | Jeevanandam |
| 5,335,668 A | 8/1994 | Nardella | 5,609,151 A | 3/1997 | Mulier et al. |
| 5,336,217 A | 8/1994 | Buys | 5,620,438 A | 4/1997 | Amplatz et al. |
| 5,336,443 A | 8/1994 | Eggers ................ 252/511 | 5,626,576 A | 5/1997 | Janssen |
| 5,342,357 A | 8/1994 | Nardella | 5,633,578 A | 5/1997 | Eggers et al. |
| 5,348,553 A | 9/1994 | Whitney | 5,643,251 A | 7/1997 | Hillsman et al. |
| 5,348,554 A | 9/1994 | Imran | 5,643,255 A | 7/1997 | Organ |
| 5,366,443 A | 11/1994 | Eggers et al. | 5,647,869 A | 7/1997 | Goble et al. |
| 5,370,642 A | 12/1994 | Keller | 5,662,124 A | 9/1997 | Wilk ................ 128/898 |
| 5,370,644 A | 12/1994 | Langberg | 5,662,680 A | 9/1997 | Desai |
| 5,370,675 A | 12/1994 | Edwards et al. | 5,669,907 A * | 9/1997 | Platt et al. ................ 606/41 |
| 5,374,261 A | 12/1994 | Yoon ................ 604/385.01 | 5,672,170 A | 9/1997 | Cho |
| 5,374,265 A | 12/1994 | Sand | 5,673,695 A | 10/1997 | McGee |
| 5,375,588 A | 12/1994 | Yoon | 5,676,693 A | 10/1997 | LaFontaine et al. |
| 5,380,277 A | 1/1995 | Phillips | 5,681,282 A | 10/1997 | Eggers et al. |
| 5,380,316 A | 1/1995 | Aita et al. | 5,681,308 A | 10/1997 | Edwards |
| 5,382,261 A | 1/1995 | Palmaz ................ 606/158 | 5,683,366 A | 11/1997 | Eggers et al. |
| 5,383,876 A | 1/1995 | Nardella | 5,697,281 A | 12/1997 | Eggers et al. |
| 5,383,917 A | 1/1995 | Desai et al. | 5,697,536 A | 12/1997 | Eggers et al. |
| 5,389,096 A | 2/1995 | Aita et al. | 5,697,882 A | 12/1997 | Eggers et al. |
| 5,391,199 A | 2/1995 | Ben-Haim ................ 607/122 | 5,697,909 A | 12/1997 | Eggers et al. |
| 5,395,312 A | 3/1995 | Desai | 5,700,262 A | 12/1997 | Acosta |
| 5,400,267 A | 3/1995 | Denen et al. ................ 702/59 | 5,725,524 A | 3/1998 | Mulier et al. |
| 5,400,428 A | 3/1995 | Grace | 5,749,914 A | 5/1998 | Janssen |
| 5,401,272 A | 3/1995 | Perkins ................ 606/15 | 5,766,153 A | 6/1998 | Eggers et al. |
| 5,403,311 A | 4/1995 | Abele | 5,766,164 A | 6/1998 | Mueller et al. ................ 606/15 |
| 5,417,687 A | 5/1995 | Nardella et al. | 5,766,192 A | 6/1998 | Zacca |
| 5,419,767 A | 5/1995 | Eggers et al. | 5,769,843 A | 6/1998 | Abela |
| 5,421,955 A | 6/1995 | Lau et al. ................ 216/48 | 5,775,338 A | 7/1998 | Hastings |
| 5,423,803 A | 6/1995 | Tankovich | 5,779,715 A | 7/1998 | Tu ................ 606/108 |
| 5,423,806 A | 6/1995 | Dale et al. | 5,807,384 A | 9/1998 | Mueller |
| 5,423,810 A | 6/1995 | Goble et al. | 5,807,395 A | 9/1998 | Mulier et al. |
| 5,423,882 A | 6/1995 | Jackman et al. | 5,810,764 A | 9/1998 | Eggers et al. |
| 5,425,355 A | 6/1995 | Kulick | 5,810,809 A | 9/1998 | Rydell |
| 5,429,144 A | 7/1995 | Wilk | 5,817,013 A | 10/1998 | Ginn |
| 5,429,604 A | 7/1995 | Hammersmark et al. | 5,823,955 A | 10/1998 | Kuck |
| 5,431,649 A | 7/1995 | Mulier et al. ................ 606/47 | 5,824,005 A | 10/1998 | Motamedi et al. ................ 606/15 |
| 5,433,708 A | 7/1995 | Nichols et al. | 5,827,203 A | 10/1998 | Nita ................ 601/2 |
| 5,436,566 A | 7/1995 | Thompson et al. | 5,836,868 A | 11/1998 | Resseman |
| 5,437,658 A | 8/1995 | Muller et al. | 5,836,875 A | 11/1998 | Webster, Jr. ................ 600/374 |
| 5,437,662 A | 8/1995 | Nardella | 5,836,946 A | 11/1998 | Diaz et al. ................ 606/45 |
| 5,438,302 A | 8/1995 | Goble | 5,840,059 A | 11/1998 | March |
| 5,441,499 A | 8/1995 | Fritzsch | 5,843,019 A | 12/1998 | Eggers et al. |
| 5,445,634 A | 8/1995 | Keller | 5,860,951 A | 1/1999 | Eggers |
| 5,451,224 A | 9/1995 | Goble et al. | 5,860,974 A * | 1/1999 | Abele ................ 606/41 |
| 5,454,809 A * | 10/1995 | Janssen ................ 606/41 | 5,860,975 A | 1/1999 | Goble et al. |
| 5,456,680 A | 10/1995 | Taylor et al. | 5,871,469 A | 2/1999 | Eggers et al. |
| 5,462,544 A | 10/1995 | Sakesena | 5,873,855 A | 2/1999 | Eggers et al. |
| 5,464,404 A | 11/1995 | Abela | 5,885,277 A | 3/1999 | Korth |
| 5,476,505 A | 12/1995 | Limon ................ 623/1 | 5,888,198 A | 3/1999 | Eggers et al. |
| 5,484,433 A | 1/1996 | Taylor et al. | 5,891,095 A | 4/1999 | Eggers et al. |
| 5,487,385 A | 1/1996 | Avitall | 5,891,133 A | 4/1999 | Murphy-Chutorian ................ 606/7 |
| 5,496,312 A | 3/1996 | Klicek | 5,891,134 A | 4/1999 | Goble et al. ................ 606/27 |
| 5,496,314 A | 3/1996 | Eggers | 5,891,140 A | 4/1999 | Ginn et al. ................ 606/48 |
| 5,496,317 A | 3/1996 | Goble et al. | 5,893,848 A | 4/1999 | Negus et al. ................ 606/41 |
| 5,500,012 A | 3/1996 | Brucker | 5,893,885 A | 4/1999 | Webster, Jr. |
| 5,505,725 A | 4/1996 | Samson | 5,897,553 A | 4/1999 | Mulier |
| 5,507,771 A | 4/1996 | Gianturco | 5,902,272 A | 5/1999 | Eggers et al. |
| 5,514,128 A | 5/1996 | Hillsman et al. | 5,902,289 A | 5/1999 | Swartz et al. ................ 604/530 |
| 5,514,130 A | 5/1996 | Baker | 5,910,150 A | 6/1999 | Saadat ................ 606/159 |
| 5,540,712 A | 7/1996 | Kleshinski et al. | 5,913,853 A | 6/1999 | Loeb et al. ................ 606/15 |
| 5,542,928 A | 8/1996 | Evans et al. | 5,944,715 A * | 8/1999 | Goble et al. ................ 606/41 |
| 5,545,161 A | 8/1996 | Imran | 5,954,716 A | 9/1999 | Sharkey et al. ................ 606/32 |
| 5,545,211 A | 8/1996 | An et al. | 5,980,515 A | 11/1999 | Tu ................ 606/41 |
| 5,554,152 A | 9/1996 | Aita et al. | 6,004,319 A | 12/1999 | Goble et al. |

| | | | | | | |
|---|---|---|---|---|---|---|
| 6,013,076 A | 1/2000 | Goble et al. | | 6,602,248 B1 | 8/2003 | Sharps et al. |
| 6,015,406 A | 1/2000 | Goble et al. | | 6,620,156 B1 | 9/2003 | Garito et al. ............... 606/50 |
| 6,024,733 A | 2/2000 | Eggers et al. | | 6,632,193 B1 | 10/2003 | Davison et al. ............ 604/22 |
| 6,027,501 A | 2/2000 | Goble et al. | | 6,632,220 B1 | 10/2003 | Eggers et al. ............... 606/41 |
| 6,032,674 A | 3/2000 | Eggers et al. ............... 128/898 | | 6,749,604 B1 | 6/2004 | Eggers et al. ............... 606/41 |
| 6,039,734 A | 3/2000 | Goble et al. | | 6,749,608 B2 | 6/2004 | Garito et al. ............... 606/45 |
| 6,047,700 A | 4/2000 | Eggers et al. ............... 128/898 | | 6,770,071 B2 | 8/2004 | Woloszko et al. ......... 606/41 |
| 6,056,746 A | 5/2000 | Goble et al. | | 6,780,178 B2 | 8/2004 | Palanker et al. ............ 600/41 |
| 6,063,079 A | 5/2000 | Hovda et al. | | 6,780,180 B2 | 8/2004 | Goble et al. ............... 606/41 |
| 6,066,134 A | 5/2000 | Eggers et al. | | 6,802,842 B2 | 10/2004 | Ellman et al. ............ 606/45 |
| 6,068,628 A | 5/2000 | Fanton et al. | | 6,837,887 B2 | 1/2005 | Woloszko et al. ......... 606/41 |
| 6,074,386 A | 6/2000 | Goble et al. | | 6,837,888 B2 | 1/2005 | Ciarrocca et al. ......... 606/41 |
| 6,090,106 A | 7/2000 | Goble et al. | | 6,855,143 B2 | 2/2005 | Davison et al. ............ 606/41 |
| 6,093,186 A | 7/2000 | Goble et al. | | 6,915,806 B2 | 7/2005 | Pacek et al. ............... 128/898 |
| 6,102,046 A | 8/2000 | Weinstein et al. | | 6,920,883 B2 | 7/2005 | Bessette et al. ............ 128/898 |
| 6,105,581 A | 8/2000 | Eggers et al. ............... 128/898 | | 6,929,640 B1 | 8/2005 | Underwood et al. ......... 606/32 |
| 6,109,268 A | 8/2000 | Thapliyal et al. | | 6,949,096 B2 | 9/2005 | Davison et al. ............ 606/41 |
| 6,117,109 A | 9/2000 | Eggers et al. | | 6,960,204 B2 | 11/2005 | Eggers et al. ............... 606/32 |
| 6,126,682 A | 10/2000 | Sharkey et al. | | 6,974,453 B2 | 12/2005 | Woloszko et al. ......... 606/41 |
| 6,142,992 A | 11/2000 | Cheng et al. | | 6,984,231 B2 | 1/2006 | Goble et al. ............... 606/37 |
| 6,149,620 A | 11/2000 | Baker et al. | | 6,991,631 B2 | 1/2006 | Woloszko et al. ......... 606/41 |
| 6,156,031 A | 12/2000 | Aita et al. ............... 606/33 | | 7,004,941 B2 | 2/2006 | Tvinnereim et al. ......... 606/41 |
| 6,159,194 A | 12/2000 | Eggers et al. | | 7,041,102 B2 | 5/2006 | Truckai et al. ............ 606/51 |
| 6,159,208 A | 12/2000 | Hovda et al. | | 7,070,596 B1 | 7/2006 | Woloszko et al. ......... 606/41 |
| 6,161,543 A | 12/2000 | Cox | | 7,090,672 B2 | 8/2006 | Underwood et al. ......... 606/41 |
| 6,168,593 B1 | 1/2001 | Sharkey et al. | | 7,094,215 B2 | 8/2006 | Davison et al. ............ 604/22 |
| 6,174,308 B1 | 1/2001 | Goble | | 7,104,986 B2 | 9/2006 | Hovda et al. ............... 606/32 |
| 6,174,309 B1 | 1/2001 | Wrublewski et al. ......... 606/45 | | 7,131,969 B1 | 11/2006 | Hovda et al. ............... 606/45 |
| 6,179,824 B1 | 1/2001 | Eggers et al. | | 7,169,143 B2 | 1/2007 | Eggers et al. ............... 606/32 |
| 6,179,836 B1 | 1/2001 | Eggers et al. | | 7,179,255 B2 | 2/2007 | Lettice et al. ............... 606/32 |
| 6,183,469 B1 | 2/2001 | Thapliyal et al. | | 7,186,234 B2 | 3/2007 | Dahla et al. ............... 604/22 |
| 6,190,381 B1 | 2/2001 | Olsen et al. | | 7,192,428 B2 | 3/2007 | Eggers et al. ............... 606/41 |
| 6,203,542 B1 | 3/2001 | Ellsberry et al. | | 7,201,750 B1 | 4/2007 | Eggers et al. ............... 606/41 |
| 6,210,402 B1 | 4/2001 | Olsen et al. | | 7,217,268 B2 | 5/2007 | Eggers et al. ............... 606/32 |
| 6,224,592 B1 | 5/2001 | Eggers et al. | | 7,270,658 B2 | 9/2007 | Woloszko et al. ......... 606/32 |
| 6,228,078 B1 | 5/2001 | Eggers et al. ............... 606/32 | | 2002/0029036 A1 | 3/2002 | Goble et al. |
| 6,228,081 B1 | 5/2001 | Goble | | 2002/0095151 A1 | 7/2002 | Dahla et al. ............... 606/41 |
| 6,234,178 B1 | 5/2001 | Goble et al. ............... 606/32 | | 2003/0013986 A1 | 1/2003 | Saadat ..................... 600/549 |
| 6,235,020 B1 | 5/2001 | Cheng et al. | | 2003/0028189 A1 | 2/2003 | Woloszko et al. ......... 604/45 |
| 6,237,604 B1 | 5/2001 | Burnside et al. ............ 128/897 | | 2003/0088245 A1 | 5/2003 | Woloszko et al. ......... 606/41 |
| 6,238,391 B1 | 5/2001 | Olsen et al. | | 2003/0130655 A1 | 7/2003 | Woloszko et al. ......... 606/45 |
| 6,254,600 B1 | 7/2001 | Willink et al. | | 2003/0158545 A1 | 8/2003 | Hovda et al. ............... 606/32 |
| 6,261,286 B1 | 7/2001 | Goble et al. | | 2003/0171743 A1 | 9/2003 | Tasto et al. ............... 606/32 |
| 6,261,311 B1 | 7/2001 | Sharkey et al. ............ 607/96 | | 2003/0208194 A1 | 11/2003 | Hovda et al. ............... 606/41 |
| 6,264,652 B1 | 7/2001 | Eggers et al. | | 2003/0208196 A1 | 11/2003 | Stone ..................... 606/41 |
| 6,270,460 B1 | 8/2001 | McCartan et al. ......... 600/459 | | 2003/0212396 A1 | 11/2003 | Eggers et al. ............... 606/41 |
| 6,277,112 B1 | 8/2001 | Underwood et al. | | 2004/0024399 A1 | 2/2004 | Sharps et al. ............... 606/32 |
| 6,280,441 B1 | 8/2001 | Ryan ..................... 606/45 | | 2004/0049180 A1 | 3/2004 | Sharps et al. ............... 606/32 |
| 6,293,942 B1 | 9/2001 | Goble et al. | | 2004/0054366 A1 | 3/2004 | Davison et al. ............ 606/45 |
| 6,296,636 B1 | 10/2001 | Cheng et al. | | 2004/0116922 A1 | 6/2004 | Hovda et al. ............... 606/41 |
| 6,296,638 B1 | 10/2001 | Davison et al. | | 2004/0127893 A1 | 7/2004 | Hovda ..................... 606/41 |
| 6,306,134 B1 | 10/2001 | Goble et al. | | 2004/0153057 A1 | 8/2004 | Davison ..................... 600/410 |
| 6,308,089 B1 | 10/2001 | von der Ruhr et al. ...... 600/338 | | 2004/0186469 A1 | 9/2004 | Woloszko et al. ......... 606/41 |
| 6,309,387 B1 | 10/2001 | Eggers et al. ............... 606/41 | | 2004/0230190 A1 | 11/2004 | Dahla et al. ............... 604/41 |
| 6,312,408 B1 | 11/2001 | Eggers et al. | | 2005/0004634 A1 | 1/2005 | Ricart et al. ............... 606/41 |
| 6,322,549 B1 | 11/2001 | Eggers et al. | | 2005/0010205 A1 | 1/2005 | Hovda et al. ............... 606/32 |
| 6,355,032 B1 | 3/2002 | Hovda et al. | | 2005/0119650 A1 | 6/2005 | Sanders et al. ............ 424/426 |
| 6,363,937 B1 | 4/2002 | Hovda et al. | | 2005/0131402 A1 | 6/2005 | Ciarrocca et al. ......... 600/450 |
| 6,364,877 B1 | 4/2002 | Goble et al. ............... 606/34 | | 2005/0187543 A1 | 8/2005 | Underwood et al. ......... 606/41 |
| 6,379,351 B1 | 4/2002 | Thapliyal et al. | | 2005/0234439 A1 | 10/2005 | Underwood ..................... 606/32 |
| 6,391,025 B1 | 5/2002 | Weinstein et al. | | 2005/0251134 A1 | 11/2005 | Woloszko et al. ......... 606/32 |
| 6,416,507 B1 | 7/2002 | Eggers et al. | | 2005/0261754 A1 | 11/2005 | Woloszko ..................... 606/32 |
| 6,416,508 B1 | 7/2002 | Eggers et al. | | 2005/0288665 A1 | 12/2005 | Woloszko ..................... 606/41 |
| 6,416,509 B1 | 7/2002 | Goble et al. ............... 606/37 | | 2006/0036237 A1 | 2/2006 | Davison et al. ............ 606/41 |
| 6,432,103 B1 | 8/2002 | Ellsberry et al. | | 2006/0095026 A1 | 5/2006 | Ricart et al. ............... 606/32 |
| 6,468,274 B1 | 10/2002 | Alleyne et al. ............ 606/32 | | 2006/0095031 A1 | 5/2006 | Ormsby ..................... 606/34 |
| 6,468,275 B1 | 10/2002 | Wampler et al. ............ 606/48 | | 2006/0129145 A1 | 6/2006 | Woloszko et al. ......... 606/41 |
| 6,482,201 B1 | 11/2002 | Olsen et al. ............... 606/41 | | 2006/0178670 A1 | 8/2006 | Woloszko et al. ......... 606/48 |
| 6,517,498 B1 | 2/2003 | Burbank et al. ............ 600/564 | | 2006/0189971 A1 | 8/2006 | Tasto et al. ............... 606/32 |
| 6,530,922 B2 | 3/2003 | Cosman | | 2006/0253117 A1 | 11/2006 | Hovda et al. ............... 128/898 |
| 6,578,579 B2 | 6/2003 | Burnside ..................... 128/897 | | 2006/0259025 A1 | 11/2006 | Dahla ..................... 607/108 |
| 6,582,423 B1 | 6/2003 | Thapliyal et al. ............ 606/32 | | 2007/0010808 A1 | 1/2007 | Dahla ..................... 606/41 |
| 6,589,237 B2 | 7/2003 | Woloszko et al. ......... 606/41 | | 2007/0010809 A1 | 1/2007 | Hovda et al. ............... 606/32 |

| | | | |
|---|---|---|---|
| 2007/0106288 A1 | 5/2007 | Woloszko et al. ............. 606/41 |
| 2007/0112346 A1 | 5/2007 | Underwood et al. .......... 606/41 |
| 2007/0112348 A1 | 5/2007 | Eggers et al. ................. 606/41 |
| 2007/0129715 A1 | 6/2007 | Eggers et al. ................. 606/32 |
| 2007/0149966 A1 | 6/2007 | Dahla et al. ................... 606/41 |
| 2007/0161981 A1 | 7/2007 | Sanders et al. ................ 606/41 |
| 2007/0179497 A1 | 8/2007 | Eggers et al. ................. 606/41 |
| 2007/0208334 A1 | 9/2007 | Woloszko et al. ............. 606/41 |
| 2007/0208335 A1 | 9/2007 | Woloszko et al. ............. 606/41 |
| 2007/0213700 A1 | 9/2007 | Davison et al. ............... 606/32 |

FOREIGN PATENT DOCUMENTS

| | | |
|---|---|---|
| DE | 3930451 | 3/1991 |
| DE | 29609350 | 5/1996 |
| DE | 19537084 | 4/1997 |
| DE | 29619029 | 4/1997 |
| EP | 182689 | 5/1986 |
| EP | 0 703 461 | 3/1996 |
| EP | 0703461 | 3/1996 |
| EP | 0553576 | 4/1996 |
| EP | 0 740 926 A2 | 11/1996 |
| EP | 0 754 437 | 1/1997 |
| EP | 0515867 | 7/1999 |
| EP | 0 694 290 | 11/2000 |
| FR | 1514319 | 8/1968 |
| FR | 2313949 | 1/1977 |
| GB | 2 308 979 | 7/1997 |
| GB | 2 308 980 | 7/1997 |
| GB | 2 308 981 | 7/1997 |
| GB | 2308979 | 7/1997 |
| GB | 2308980 | 7/1997 |
| GB | 2308981 | 7/1997 |
| GB | 2 327 350 | 1/1999 |
| GB | 2 327 351 | 1/1999 |
| GB | 2 327 352 | 1/1999 |
| JP | 57-57802 | 4/1982 |
| JP | 57-117843 | 7/1982 |
| NL | 05/000434 | 12/2006 |
| WO | 94/03134 | 2/1974 |
| WO | 90/03152 | 4/1990 |
| WO | 90/07303 | 7/1990 |
| WO | WO 90/07303 | 7/1990 |
| WO | 92/21278 | 12/1992 |
| WO | WO 92/21278 | 12/1992 |
| WO | 93/13816 | 7/1993 |
| WO | 93/20747 | 10/1993 |
| WO | WO93/20747 | 10/1993 |
| WO | WO94/03134 | 2/1994 |
| WO | 94/04220 | 3/1994 |
| WO | 94/08654 | 4/1994 |
| WO | 94/14383 | 7/1994 |
| WO | WO 94/26228 | 11/1994 |
| WO | 95/05780 | 3/1995 |
| WO | WO95/05780 | 3/1995 |
| WO | 95/34259 | 12/1995 |
| WO | WO95/34259 | 12/1995 |
| WO | 96/00042 | 1/1996 |
| WO | 96/35469 | 11/1996 |
| WO | WO 96/35469 | 11/1996 |
| WO | 96/39962 | 12/1996 |
| WO | 96/39963 | 12/1996 |
| WO | 96/39965 | 12/1996 |
| WO | WO 96/39962 | 12/1996 |
| WO | WO 96/39964 | 12/1996 |
| WO | WO 96/39965 | 12/1996 |
| WO | 97/00646 | 1/1997 |
| WO | 97/00647 | 1/1997 |
| WO | WO 97/00646 | 1/1997 |
| WO | WO97/00647 | 1/1997 |
| WO | 97/18768 | 5/1997 |
| WO | 97/24073 | 7/1997 |
| WO | 97/24074 | 7/1997 |
| WO | 97/24993 | 7/1997 |
| WO | 97/24994 | 7/1997 |
| WO | 97/25101 | 7/1997 |
| WO | WO 97/24073 | 7/1997 |
| WO | WO 97/24993 | 7/1997 |
| WO | WO 97/24994 | 7/1997 |
| WO | 97/34540 | 9/1997 |
| WO | 97/44071 | 11/1997 |
| WO | 97/48345 | 12/1997 |
| WO | 97/48346 | 12/1997 |
| WO | WO 97/48346 | 12/1997 |
| WO | 98/07468 | 2/1998 |
| WO | 98/17185 | 4/1998 |
| WO | 98/17186 | 4/1998 |
| WO | 98/19614 | 5/1998 |
| WO | 98/23324 | 6/1998 |
| WO | 98/27877 | 7/1998 |
| WO | 98/27879 | 7/1998 |
| WO | 98/27880 | 7/1998 |
| WO | 98/30144 | 7/1998 |
| WO | 98/38925 | 9/1998 |
| WO | 98/39038 | 9/1998 |
| WO | 98/56324 | 12/1998 |
| WO | 99/09919 | 3/1999 |
| WO | 99/49799 | 10/1999 |
| WO | 99/51155 | 10/1999 |
| WO | 99/51158 | 10/1999 |
| WO | 01/87154 | 5/2001 |
| WO | 02/36028 | 5/2002 |
| WO | 93/13816 | 7/2003 |
| WO | 2005/125287 | 12/2005 |

OTHER PUBLICATIONS

P.C. Nardella (19889) *SPIE* 1068:42-49 Radio Frequency Energy and Impedance Feedback.
Band et al. (1985) *J. Arthro. Surg.* 1:242-246 Effect of Electrocautery on Fresh Human Articular Cartilage.
Satler, L.F. (1996) *Catheterization and Cardiovascular Diagnosis* 37:320-321. "Remedies" for In-Stent Restenosis.
Topaz, O., et al. (1996) *Catheterization and Cardiovascular Diagnosis* 37:293-299. The Stenotic Stent: Mechanisms and Revascularization Options.
Pearce, John A. (1986) *Electrosurgery*, pp. 17, 69-75, 87, John Wiley & Sons, New York.
J.W. Ramsey et al. *Urological Research* vol. 13, pp. 99-102 (1985).
V.E. Elasasser et al. *Acta Medicotechnica* vol. 24, No. 4, pp. 129-134 (1976).
P.C. Nardella (1989) *SPIE* 1068: 42-49 Radio Frequency Energy and Impedance Feedback.
R. Tucker et al. *J. of Urology* vol. 141, pp. 662-665, (1989).
R. Tucker et al. *Urological Research* vol. 18, pp. 291-294 (1990).
Knamolowsky et al. *J. of Urology* vol. 143, pp. 275-277 (1990).
Kramolowsky et al. *J. of Urology* vol. 146, pp. 669-674 (1991).
Slager et al. *Z. Kardiol.* 76:Suppl. 6, 67-71 (1987).
Slager et al. *JACC* 5(6):1382-6 (1985).
Olsen MD, Bipolar Laparoscopic Cholecstectomy Lecture (marked confidential), Oct. 7, 1991.
Codman & Shurtleff, Inc. "The Malis Bipolar Electrosurgical System CMC-III Instruction Manual" Jul. 1991.
Valley Forge's New Products, CLINICA, 475, 5, Nov. 6, 1991.
Valley Forge Scientific Corp., "Summary of Safety and Effective Information from 510K," 1991.
Codman & Shurtleff, Inc. "The Malis Bipolar Coagulating and Bipolar Cutting System CMC-II" brochure, early 1991.
L. Malis, "The Value of Irrigation During Bipolar Coagulation" See ARTC 21602, early Apr. 9, 1993.
L. Malis, "Excerpted from a seminar by Leonard I. Malis, M.D. at the 1995 American Association of Neurological Surgeons Meeting," 1995.

L. Malis, "Electrosurgery, Technical Note," *J. Neursurg.*, vol. 85, 970-975, Nov. 1996.

Ian E. Shuman, "Bipolar Versus Monopolar Electrosurgery: Clinical Applications," *Dentistry Today*, vol. 20, No. 12, Dec. 2001.

Cook and Webster, "Therapeutic Medical Devices: Application and Design," 1982.

Valleylab SSE2L Instruction Manual, Jan. 6, 1983.

Robert D. Tucker et al., "Demodulated Low Frequency Currents from Electrosurgical Procedures," *Surgery, Gynecology and Obstetrics*, 159:39-43, 1984.

Selikowitz & LaCourse, "Electric Current and Voltage Recordings on the Myocardium During Electrosurgical Procedures in Canines," *Surgery, Gynecology & Obstetrics*, vol. 164, 219-224, Mar. 1987.

J. O'Malley, Schaum's Outline of Theory and Problems of Basic Circuit pp. 3-5, 1992.

Arnaud Wattiez et al., "Electrosurgery in Operative Endoscopy," Electrosurgical Effects, Blackwell Science, pp. 85-93, 1995.

Leslie A. Geddes, "Medical Device Accidents: With Illustrative Cases" CRC Press, 1998.

C.P. Swain, et al., *Gut* vol. 25, pp. 1424-1431 (1984).

Piercey et al., *Gastroenterology* vol. 74(3), pp. 527-534 (1978).

A.K. Dobbie *Bio-Medical Engineering* vol. 4, pp. 206-216 (1969).

B. Lee et al. *JACC* vol. 13(5), pp. 1167-1175 (1989).

K. Barry et al. *American Heart Journal* vol. 117, pp. 332-341 (1982).

W. Honig *IEEE* pp. 58-65 (1975).

Jacob Kline, *Handbook of Biomedical Engineering*, Academic Press Inc., N.Y., pp. 98-113, 1988.

Letter from Department of Health to Jerry Malis dated Apr. 15, 1985.

Letter from Jerry Malis to FDA dated Jul. 25, 1985.

Letter from Department of Health to Jerry Malis dated Apr. 22, 1991.

Leonard Malis, "Instrumenation for Microvascular Neurosurgery" *Cerebrovascular Surgery*, vol. 1, 245-260, 1985.

Valleylab, Inc. "Valleylab Part No. 945 100 102 A" Surgistat Service Manual, Jul. 1988.

Leonard I. Malis, "New Trends in Microsurgery and Applied Technology," *Advanced Technology in Neurosurgery*, 1-16, 1988.

Regional myocardial blood flow and cardiac mechanics in dog hearts with $CO_2$ laser-induced intramyocardial revascularization, Basic Research in Cardiology 85:179-197 (1990) R. Hardy, F. James, R Millard and S. Kaplan.

Transventricular Revascularization by Laser, Lasers in Surgery and Medicine 2:187-198 (1982) M. Mirhoseini MD, Muckerheide, and Cayton RN.

Transmyocardial Laser Revascularization: A Review; J. Of Clinical Laser Medicine & Surgery V. 11, No. 1 1993 pp. 15-19; M. Mirhoseini, MD, S. Shelgikar MD, M Cayton RN.

Transmural Channels Can Protect Ischemic Tissue; Circulation vol. 93 No. 1, Jan. 1, 1996; P. Whittaker, PhD; Karel Rakusan, MD, Ph.D; Robert Kloner, MD, PhD.

Treatment of Acute Myocardial Infarction by Transmural Blood Supply from the Ventricular Cavity; Europ. Surg. Res. 3; 130-138 (1971) P. Walter, H. Hundeshagen and H.G. Borst.

Dennis et al. "Evolution of Electrofulguration in Control of Bleeding of Experimental Gastric Ulcers," Digestive Diseases and Sciences, vol. 24, No. 11, 845-845, Nov. 1979.

Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 01, 1987.

Protell et al., "Computer-Assisted Electrocoagulation: Biopolar v. Monopolar in the Treatment of Experimental Canine Gastric Ulcer Bleeding," *Gastroenterology* vol. 80, No. 3, pp. 451-455, 1981.

Stoffels, E. et al., "Investigation on the Interaction Plasma-Bone Tissue", E-MRS Spring Meeting, 1 pg, Jun. 18-21, 2002.

Stoffels, E. et al., "Biomedical Applications of Plasmas", Tutorial presented prior to the 55th Gaseous Electronics Conference in Minneapolis, MN, 41 pgs, Oct. 14, 2002.

Stoffels, E. et al., "Plasma Interactions with Living Cells", Eindhoven University of Technology, 1 pg, Nov. 28, 2002.

Stoffels, E. et al., "Superficial Treatment of Mammalian Cells using Plasma Needle", J. Phys. D: Appl. Phys. 26, pp. 2908-2913, Nov. 19, 2003.

Stoffels, E. et al., "Plasma Needle", Eindhoven University of Technology, 1 pg, Nov. 28, 2003

Stoffels, E. et al., "Plasma Physicists Move into Medicine", Physicsweb, 1 pg, Nov. 2003.

Stoffels, E. et al., "Plasma Treated Tissue Engineered Skin to Study Skin Damage", Biomechanics and Tissue Engineering, Materials Technology, 1 pg, 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction of Plasma Science, vol. 32, No. 4, pp. 1544-1550, Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs, 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al. "Deactivation of *Escherichia Coli* by the Plasma Needle", J. Phys. D: Appl. Phys. 38, pp. 1716-1721, May 20, 2005.

Stoffels E. et al., "Development of a Gas Plasma Catheter for Gas Plasma Surgery", XXVIIth ICPIG, Endoven University of Technology, pp. 18-22, Jul. 2005.

Stoffels. E. et al., "Development of a Smart Positioning Sensor for the Plasma Needle", Plasma Sources Sci. Technol. 15, pp. 582-599, Jun. 27, 2006.

Stoffels, E. et al., Killing of S. Mutana Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia Coli* and Streptococcus Mutans", IEEE Transaction on Plasma Science, vol. 34, No. 4, pp. 1325-1330, Aug. 2006.

Stoffels, E. et al., "Reattahcment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for In Vivo Medical Treatment: Recent Developments and Perspectives", Plasma Sources Sci. Technol. 15, pp. S169-S180, Oct. 06, 2006.

Tucker, R. et al., Abstract P14-11, p. 248, "A Bipolar Electrosurgical Turp Loop", Nov. 1989.

Wyeth, "Electrosurgical Unit" pp. 1181-1202.

Mirhoseini et al., "New Concepts in Revascularization of the Myocardium", Ann Thorac Surg 45:415-420, 1988.

Mirhoseini et al., "Revascularization of the heart by Laser", J. of Microsurgery 2:253-260, 1981.

Rand et al., "Effect of Elecctrocautery on Fresh Human Articular Cartilage", J. Arthro. Surg., vol. 1, pp. 242-246, 1985, 1985.

Satler, L.F., "Remedies for In-Stent Restenosis", Catheterization and Cardiovascular Diagnosis 37:320-321, 1996.

Sen, J. et al., "Transyocardial Acupuncture", Thoracic and Cardiovascular Surgery 50(2): 181-1289, (1965), 1965.

Topaz, O., "The Stenotic Stent: Mechanisms and Revascularization Options", Catheterization and Cardiovascular Diagnosis 37:293-299, 1996

Euroepean Search Report for EP 01127084 3pgs, Mailed Oct. 7, 2003, Mailed Oct. 7, 2003.

PCT International Search Report for PCT/US92/11265 1 page, Mailed Jun. 11, 1993.

PCT Written Opinion for PCT/US92/11265 4 pgs, Mailed Jul. 8, 1994.

PCT Notification of Transmittal of the International Search Report for PCT/US96/18651 4 pgs, Mailed Jan. 30, 1997.

PCT Notification of Transmittal of the International Preliminary Examination Report for PCT/US96/18651 4 pgs, Mailed Sep. 22, 1997.

PCT Notification of Transmittal of the International Search Report for PCT/US98/07976 4 pgs, Mailed Aug. 20, 1998.

PCT Notification of Transmittal of the International Preliminary Examination Report for PCT/US98/07976 4 pgs, Mailed Jun. 9, 1999.

PCT Notification of Transmittal of the International Search Report for PCT/US98/07976 4 pgs, Mailed Nov. 12, 1998.

PCT Written Opinion for PCT/US98/17703 5 pgs, Mailed Aug. 11, 1999.

PCT Notification of Transmittal of the International Search Report for PCT/US99/06808 4 pgs, Mailed May 27, 1999.

PCT Written Opinion for PCT/US99/06808 4 pgs, Mailed Jan. 18, 2000.

* cited by examiner

ELECTROSURGICAL SYSTEM FOR TREATING RESTENOSIS OF BODY LUMENS

This application is a divisional and claims the benefit of U.S. application Ser. No. 08/874,173 filed Jun. 13, 1997, now U.S. Pat. No. 6,179,824, the disclosure of which is incorporated by reference.

CROSS-REFERENCE TO RELATED APPLICATIONS

The present invention is related to commonly assigned U.S. patent applications Ser. No. 08/561,958, filed on Nov. 22, 1995, now U.S. Pat. No. 5,697,882; Ser. No. 08/485,219 filed Jun. 7, 1995, now U.S. Pat. No. 5,697,281; which was a continuation-in-part of PCT International Application, U.S. National Phase Serial No. PCT/US94/05168 filed May 10, 1994; which was a continuation-in-part of U.S. patent application Ser. No. 08/059,681, filed on May 10, 1993, now abandoned; which was a continuation-in-part of U.S. application Ser. No. 07/958,977, filed on Oct. 9, 1992, now U.S. Pat. No. 5,366,443; which is a continuation-in-part of U.S. application Ser. No. 07/817,575, filed on Jan. 7, 1992, now abandoned, the full disclosures of which are incorporated herein by reference.

BACKGROUND OF THE INVENTION

Field of the Invention

The present invention relates generally to apparatus and methods for maintaining patency in body passages and more particularly to a catheter system capable of selectively ablating occlusive media within a body lumen. The present invention is particularly useful for the electrosurgical cutting or ablation of invasive tissue growth in and around a stent anchored in the body lumen to help reduce or eliminate restenosis of the body lumen.

When a patient is suffering from atherosclerosis, significant occlusions or blockages are formed on the interior wall of the artery. As a result of these occlusions, the organ or extremity to which blood is to be supplied is compromised and the patient may experience a myocardial infarction or stroke. In less severe cases, it is often sufficient to treat the symptoms with pharmaceuticals and lifestyle modification to lessen the underlying causes of the disease. In more severe cases, a coronary artery blockage can often be treated using endovascular techniques such as balloon angioplasty, atherectomy, laser or hot tip ablation, placement of stents, and the like.

Percutaneous transluminal balloon angioplasty (PTBA) has become a recognized method of reducing the occlusion of blood vessels. The procedure involves routing a catheter having an inflatable balloon at the distal end thereof through the vascular system until the balloon is positioned at the site of the stenotic lesion to be treated. The balloon is then inflated to compress the atherosclerotic plaque into the wall of the blood vessel, thus increasing the size of the opening and enhancing blood flow through the affected artery. However, this successful procedure is overshadowed by the occurrence of restenosis, a re-narrowing of the artery. Studies have shown that 30-40 percent of angioplasty patients experience restenosis within 3-6 months of the angioplasty procedure. When restenosis occurs, patients may be treated with cardiovascular medications, additional angioplasty procedures or bypass surgery.

Restenosis often occurs because the wall of the dilated artery tends to spring back to its original shape following deflation of the dilation balloon. Arterial stenting has been introduced as a solution to the recoil of the vessel wall. Arterial stenting involves the placement of an expandable coil spring or wire-mesh tube within the occluded artery to reopen the lumen of the blood vessel. One example of an arterial stent is disclosed in U.S. Pat. No. 4,739,792 to Julio Palmaz. The Palmaz device comprises an expandable wire-mesh graft or prosthesis which is mounted upon an inflatable balloon catheter. The catheter assembly, including the graft, is delivered to the occluded area and is then inflated to radially force the graft into contact with the occlusion. As the graft expands, the lumen of the blood vessel is opened and blood flow is restored. After complete expansion of the graft, the balloon catheter is deflated and removed, leaving behind the graft to buttress and prevent elastic recoil of the blood vessel wall.

Although this method is successful in preventing recoil of the vessel wall, restenosis will often still occur. Smooth muscle cells which form the vessel wall tend to proliferate and build-up in the newly stented area of the blood vessel. This cellular build-up may eventually become large enough to block the lumen of the blood vessel.

It has recently been determined that localized heating of the blood vessel wall may inhibit the proliferation of smooth muscle cells which are believed to cause restenosis. One example of localized blood vessel heating is disclosed in U.S. Pat. No. 4,799,479 to Spears. The Spears patent discloses an apparatus for angioplasty having an inflatable balloon catheter which is provided with a meshwork of electrical wires to supply heat to a vessel wall. Following balloon angioplasty, the external surface of the balloon is heated to fuse together disrupted tissue elements and to kill smooth muscle cells which are believed to lead to restenosis. Unfortunately, the Spears device does not adequately prevent the spontaneous elastic recoil of the arterial wall. Immediately following angioplasty, the arterial wall begins to spring back to its original shape.

Thus stenting in and of itself is ineffective in preventing restenosis due to the occurrence of cellular proliferation. Likewise, balloon dilation in combination with localized heating does not adequately prevent restenosis since the vessel wall tends to spontaneously return to its original occluded shape.

Other techniques have recently been developed to help reduce incidences of restenosis. For example, procedures for irradiating the angioplasty-site with UV light to reduce the proliferation of smooth muscle cells at the site have been disclosed. In addition, techniques have been disclosed for the controlled application of thermal and/or electrical energy directly to the stent by, for example, including resistive or inductive heating elements that may include radiofrequency electrodes within the stent. The radiofrequency energy is then applied to the stent to disrupt the cellular growth in or around the stent. One major disadvantage of these procedures is that it is difficult to selectively apply the energy to the invasive tissue without causing thermal damage to the body lumen wall. In particular, methods that apply energy, such as RF energy, directly to the stent will often cause thermal damage to the surrounding body lumen in which the stent is anchored.

SUMMARY OF THE INVENTION

The present invention comprises apparatus and methods for maintaining patency in body passages subject to occlusion by invasive tissue growth. The apparatus and methods of the present invention may be used to open and maintain patency in virtually any hollow body passage which may be subject to occlusion by invasive cellular growth or invasive solid tumor growth. Suitable hollow body passages include ducts, orifices, lumens, and the like, with exemplary body passages including the coronary arteries. The present invention is particularly useful for reducing or eliminating the effects of restenosis in coronary arteries by selectively removing tissue ingrowth in or around stents anchored therein.

The principles of the present invention are generally applicable to any body lumen which becomes partially or totally occluded. The present invention is particularly useful in a lumen containing a lumenal prosthesis, such as a stent, stent-graft or graft, which may be metallic, non-metallic or a non-metallic coated metallic structure. Restenosis often occurs when arthermateous media or thrombus moves or grows through or around the cylindrical wall of the prosthesis to partially occlude the body passage. Methods of the present invention comprise advancing an electrosurgical catheter within the body passage such that an electrode terminal is positioned near the occlusive media. High frequency voltage is applied to one or more electrode terminal(s) at the distal end of the catheter such that an electrical current flows from the electrode terminals( ), through the region of the occlusive media and to the return electrode to selectively remove the occlusive media without directly applying thermal or electrical energy to the prothesis or the lumenal wall. The electrode terminal is then advanced through the vacancy left by the removed occlusive media to recanalize the vessel. By selectively removing the occlusive media without passing energy directly to the stent, thermal damage to the surrounding lumenal wall is minimized.

A particular advantage of the present invention is the confinement of current flow paths between the return electrode and one or more electrode terminals to the vicinity of tissue ablating region. This confinement of current flow paths minimizes the undesired flow of current through portions or all of the stent, which may otherwise induce non-specific tissue injury beyond the site of recanalization of the occluded lumen. In one configuration, the return electrode is a movable guide wire positioned radially inward from the electrode terminal such that the electrical current flows from the electrode terminal radially inward to the return electrode, thereby inhibiting current flow through the prosthesis. In another embodiment, the return electrode is an annular band positioned proximal of the electrode terminal(s).

In preferred embodiments, the high frequency voltage is applied in the presence of electrically conducting fluid such that a current flow path is generated between the electrode terminal(s) and the return electrode through the electrically conducting fluid. Preferably, the electrically conductive fluid is delivered through an internal lumen in the catheter (or through a separate instrument) to a region around the occlusive media to displace naturally occurring bodily fluids. This region is then fluidly isolated to confine the electrically conducting fluid around the tissue ablation site. In one embodiment, the region is isolated by advancing proximal and distal balloons to either side of the region, and inflating these balloons to effect a seal with the interior wall of the body passage.

Once the target site is isolated from the rest of the vasculature, the supply of electrically conductive fluid is continuously delivered to the region and balanced with the aspiration of fluid from the site of intended recanalization. The electrode terminal(s) are energized by applying a high frequency voltage between electrode terminal(s) and the return electrode, which can be a movable guide wire. A high electric field is created at the surface of the electrode(s) which causes the volumetric removal or ablation or target tissue in close proximity with the electrode terminal(s). As the occlusive media is ablated, gaseous products are generated which are entrained in the electrically conducting fluid and removed through the aspiration lumen in the catheter. The current flux lines are generally confined to the central portion of tissue ablation region because they generally flow inward towards the return electrode and because the occlusive media generally shields the outer region of the body passage (including the stent) from the current flux lines. This minimizes undesirable interaction between the electrical current and the stent. In an exemplary embodiment, the distal portion of the catheter body is reciprocally rotated as the electrode terminal is energized to selectively ablate the occlusive media. The catheter body is then advanced through the vacancy left by the ablated occlusive media to recanalize the vessel.

In a specific aspect of the invention, the high frequency voltage applied between the electrode terminal(s) and the return electrode generates high voltage gradients in the vicinity of the electrode terminals. These high voltage gradients are sufficient to create an electric field at the distal boundary of these electrodes(s) that is sufficiently high to break down the occlusive media through molecular dissociation or disintegration. The high frequency voltage imparts energy to the target site to ablate a thin layer of tissue without causing substantial tissue necrosis beyond the boundary of the occlusive media within the body passage. This ablative process can be precisely controlled to effect the volumetric removal of the occlusive media within a small blood vessel with minimal heating of, or damage to, the surrounding stent and lumenal wall.

A further understanding of the nature and advantages of the invention will become apparent by reference to the remaining portions of the specification and drawings.

DESCRIPTION OF THE PREFERRED EMBODIMENT

Figure 1:
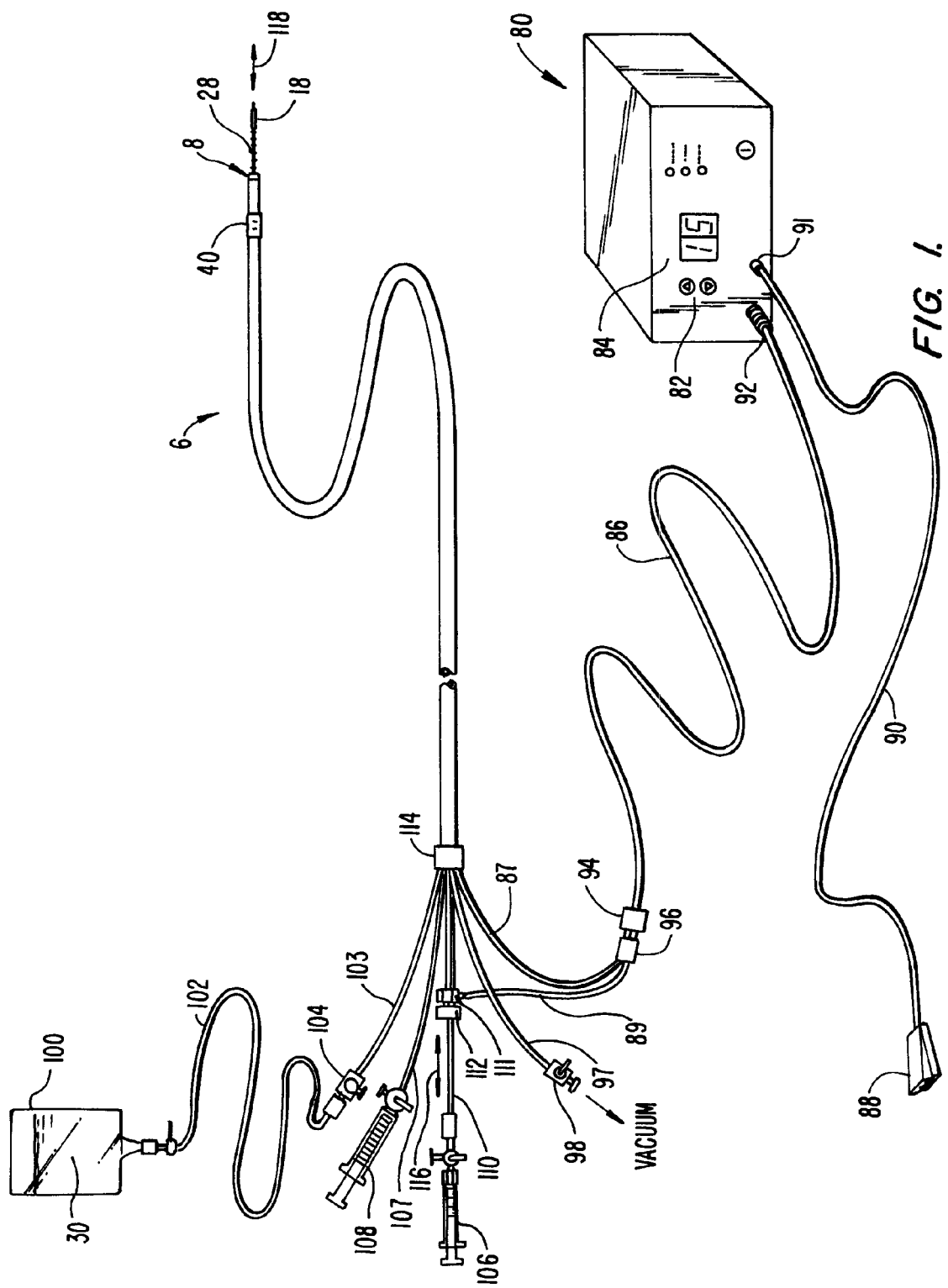
FIG. 1 schematically illustrates a lumen recanalization catheter system according to the present invention.

The present invention provides systems and methods for selectively applying electrical energy to a target location within or on a body lumen, particularly including atheromatous material which partially or fully occludes a blood vessel or other body lumen. In addition to blood vessels, body lumens that may be treated by the method and apparatus of the present invention include the urinary tract (which for example may be occluded by an enlarged prostrate in males), the fallopian tubes (which may be occluded and cause infertility), and the like. Exemplary solid tissues include abdominal tissues, neurological tissues, benign and malignant solid tumors, myocardial tissue and the like. Thus, the methods and apparatus may be used in a wide variety of procedures, including intravascular, urological, laparoscopic, arthroscopic, thoracoscopic, orthopedic, gynecologic, electrothermal, lithotripsy, spinal disc ablation, and the like. For convenience, the remaining disclosure will be directed specifically to the intravascular treatment of blood vessels but it should be appreciated that the apparatus and methods can be applied to other body lumens and passages as well as solid tissue sites for a variety of purposes.

The stenotic material in blood vessels will be, by way of example but not limited to, atheroma or atheromatous plaque. It may be relatively soft (fresh) or it may be calcified and hardened. The invention applies heat selectively to the stenotic material while limiting unwanted heating of the blood, the surrounding vessel wall and the stent anchored therein. More particularly, the present invention confines the current flow paths between the return electrode and electrode terminals to the vicinity of the tissue ablating region. This confinement of current flow paths minimizes the undesired flow of current through portions or all of the stent, which may otherwise induce non-specific tissue injury beyond the site of recanalization of the occluded lumen.

The present invention may use a single active electrode or an electrode array distributed over a distal contact surface of a catheter. The electrode array usually includes a plurality of independently current-limited and/or power-controlled electrode terminals to apply electrical energy selectively to the target tissue while limiting the unwanted application of electrical energy to the surrounding tissue and environment (e.g., the stent and the lumenal wall). The electrode terminals may be independently current-limited by isolating the terminals from each other and connecting each terminal to a separate power source or current or power limiting element (e.g., inductor) that is isolated from the other electrode terminals. Alternatively, the electrode terminals may be connected to each other at either the proximal or distal ends of the probe to form a single wire that couples to a power source.

The electrosurgical catheter will comprise a flexible body having a proximal end and a distal end which supports one or more electrode terminals. The electrode terminal(s) are preferably supported by an inorganic insulating support positioned near the distal end of the catheter body. The return electrode may be part of the catheter body, part of a separate movable guide wire or on another instrument. In the preferred embodiments, the return electrode comprises a separate movable guide wire positioned within an internal lumen of the catheter body. The proximal end of the catheter will include the appropriate electrical connections for coupling the return electrode and the electrode terminal(s) to a high frequency power supply, such as an electrosurgical generator.

The catheter will also include other internal lumens for providing separate functions, such as delivering fluid and aspirating products of ablation from the target site. Preferably, the catheter will have a fluid delivery lumen for delivering electrically conducting fluid to the target site, and an aspiration lumen coupled to a vacuum source for aspirating non-condensible gases and other products of ablation from the site.

The catheter will also preferably include an isolation system for fluidly isolating the region around the target site. In one embodiment, the isolation system includes proximal and distal balloons that are movable to portions of the body passage proximal and distal to the region of the target site. The distal balloon, by way of example, may be formed on a hollow guide wire that is fluidly coupled to an inflation source, such as a syringe. The proximal balloon, for example, may be coupled to the catheter body proximal to the active and return electrodes.

The invention typically includes guiding apparatus for guiding the catheter along a pathway approximating the central region of the occluded blood vessel. The guiding apparatus is usually an electrically conducting wire that may serve as the return electrode. The electrically conducting wire is extensible from the tip of the catheter and is located within and concentric to the catheter conveniently being in the form of a movable or fixed guidewire, usually being a movable guidewire.

The electrode array may include only one electrode terminal, or it may include at least two isolated electrode terminals, sometimes at least four electrode terminals, sometimes at least six electrode terminals, and often 50 or more electrode terminals, disposed over the distal contact surfaces on the catheter. By bringing the electrode array(s) on the contact surface(s) in close proximity with the target tissue (e.g., occlusive media) and applying high frequency voltage between the array(s) and an additional return electrode in direct or indirect contact with the patient's body, the target tissue is selectively ablated or cut, permitting selective removal of portions of the target tissue while desirably minimizing the application of energy to the surrounding stent and lumenal wall.

In an exemplary embodiment, each individual electrode terminal in the electrode array is electrically insulated from all other electrode terminals in the array and is connected to a power source which is isolated from each of the other electrodes in the array or to circuitry which limits or interrupts current flow to the electrode when low resistivity material (e.g., blood or electrically conductive saline irrigant) causes a lower impedance path between the return electrode and the individual electrode terminal. The isolated power sources for each individual electrode may be separate power supply circuits having internal impedance characteristics which limit power to the associated electrode terminal when a low impedance return path is encountered, may be a single power source which is connected to each of the electrodes through independently actuatable switches or may be provided by independent current or power limiting elements, such as inductors, capacitors, resistors and/or combinations thereof. The current or power limiting elements may be provided in the probe, connectors, cable, controller or along the conductive path from the controller to the distal tip. A more complete description of a system and method for selectively limiting current and power to an array of isolated electrode terminals can be found in commonly assigned, co-pending application Ser. No. 08/561,958, filed Nov. 22, 1995, the complete disclosure of which is incorporated herein by reference for all purposes.

In a preferred aspect, this invention takes advantage of the differences in electrical resistivity between the target occlusive media and the surrounding conductive liquid (e.g., isotonic saline irrigant, blood or the like). By way of example, for any selected level of applied voltage, if the electrical conduction path between the return electrode and one of the individual electrode terminals within the electrode array is blood (having a relatively low electrical impedance), the current control means connected to the individual electrode will limit current flow so that the heating of intervening conductive fluid is minimized. On the other hand, if a portion of or all of the electrical conduction path between the common or return electrode and one of the individual electrode terminals within the electrode array is occlusive media (having a relatively higher electrical impedance), the current control circuitry or switch connected to the individual electrode will allow current flow sufficient for the deposition of electrical energy and associated ablation or electrical breakdown of the target tissue in the immediate vicinity of the electrode surface.

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the catheter may incorporate a single electrode that extends directly through the catheter shaft or is connected to a single lead that extends to the power source.

In the case of a single electrode, the invention may also use current limiting means to apply electrical energy selectively to the target tissue while limiting the unwanted application of electrical energy to the surrounding tissue.

In this embodiment, the electrode may be connected to current limiting elements or to circuitry which limits or interrupts current flow to the electrode when low resistivity material (e.g., blood or electrically conductive saline irrigant) causes a lower impedance path between the return electrode and the electrode. The current limiting elements or circuitry may be configured to completely interrupt or modulate current flow to the electrode, for example, when a certain percentage of the electrode surface is in contact with low resistivity material. In one embodiment, the current flow will be modulated or completely interrupted when, for example, a large portion of the electrode surface is exposed to electrically conductive fluids and, therefore, not in sufficiently close proximity or contact with the target tissue. In this manner, current can be selectively applied to the target tissue, while minimizing current flow to surrounding fluids and adjacent non-target tissue structures.

In addition to the above described methods, the applicant has discovered another mechanism for ablating tissue while minimizing the depth of necrosis. This mechanism involves applying a high frequency voltage between the active electrode surface and the return electrode to develop high electric field intensities in the vicinity of the target tissue site. In this embodiment, the active electrode(s) include at least one active portion having a surface geometry configured to promote substantially high electric field intensities between the active portion and the target site when a high frequency voltage is applied to the electrodes. These high electric field intensities are sufficient to break down the tissue by processes including molecular dissociation or disintegration. The high frequency voltage imparts energy to the target site to ablate a thin layer of tissue without causing substantial tissue necrosis beyond the boundary of the thin layer of tissue ablated. This ablative process can be precisely controlled to effect the volumetric removal of tissue with minimal heating of or damage to the surrounding stent and tissue structures, such as the lumenal wall.

In an exemplary embodiment, the high electric field intensities at the active portion of the active electrode(s) may be generated by positioning the active electrode and target site within an electrically conducting fluid, such as isotonic saline or the naturally occurring body fluids in a blood vessel, such as blood, and applying a high frequency voltage that is sufficient to vaporize the electrically conducting fluid over at least a portion of the surface of the active electrode in the region between the active portion of the active electrode and the target tissue. Since the vapor layer or vaporized region has a relatively high electrical impedance, it increases the voltage differential between the active electrode tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. A more detailed description of this phenomena can be found in application Ser. No. 08/561,958, filed on Nov. 22, 1995, the complete disclosure of which has already been incorporated herein by reference.

Suitable electrode surface geometries for producing sufficiently high electric field intensities to reach the threshold conditions for vapor layer formation may be obtained by producing sharp edges, discontinuities, and/or corners at the active portion of the active electrode(s). Alternatively, the electrode(s) may be specifically designed to increase the edge/surface area ratio of the active portion through the use of shaped wires (e.g., square or hexagonal wires) or tubular electrodes offering high electric field intensities along the inside and outside perimeters of the tubular electrode. Additionally or alternatively, the active electrode surface(s) may be modified through chemical, electrochemical or abrasive methods to create a multiplicity of surface aspirates on the electrode surface. Suitable electrode designs for use with the present invention may be found in co-pending, commonly assigned application Ser. No. 08/687,792, filed Jul. 19, 1996, the complete disclosure of which is incorporated herein by reference.

The voltage applied between the return electrode and the electrode array will be at high or radio frequency, typically between about 5 kHz and 20 MHz, usually being between about 30 kHz and 2.5 MHz, and preferably being between about 50 kHz and 1 MHz. The RMS (root mean square) voltage applied will usually be in the range from about 5 volts to 1000 volts, preferably being in the range from about 50 volts to 800 volts, and more preferably being in the range from about 60 volts to 500 volts. These frequencies and voltages will result in peak-to-peak voltages and current that are sufficient to vaporize the electrically conductive fluid and, in turn, create the conditions within the vaporized region which result in high electric fields and emission of energetic photons and/or electrons to ablate tissue. Typically, the peak-to-peak voltage will be in the range of 40 to 4000 volts and preferably in the range of 100 to 3200 volts and more preferably in the range of 300 to 2400 volts.

As discussed above, the voltage is usually delivered in a waveform having a sufficiently high frequency (e.g., on the order of 5 kHz to 20 MHz) such that the voltage is effectively applied continuously (as compared with e.g., lasers claiming small depths of necrosis, which are generally delivered in brief pulses at a repetition rate of about 10 to 20 Hz). Hence, the duty cycle (i.e., cumulative time in any one-second interval that energy is applied) is on the order of about 50% for the present invention, as compared with lasers which typically have a duty cycle of about 0.001% to 0.0001%.

Usually, the current level will be selectively limited or controlled and the voltage applied will be independently adjustable, frequently in response to the resistance of tissues and/or fluids in the pathway between an individual electrode and the return electrode. Also, the applied voltage level may be in response to a temperature control means which maintains the target tissue temperature within desired limits at the interface between the electrode arrays and the target tissue. The desired tissue temperature along a propagating surface just beyond the region of ablation will usually be in the range from about 40° C. to 100° C., and more usually from about 50° C. to 60° C. The tissue being ablated (and hence removed from the operation site) immediately adjacent the electrode array may reach even higher temperatures. A temperature sensor may be incorporated within the distal end of the electrosurgical device to measure a temperature indicative of the nearby tissue beyond the ablation boundary.

Referring to the drawings in detail, wherein like numerals indicate like elements, a lumen recanalization catheter system 2 is shown constructed according to the principles of the present invention. Catheter system 2 generally comprises an electrosurgical catheter 6 connected to a power supply 80 by an interconnecting cable 86 for providing high frequency voltage to a target tissue and an irrigant reservoir or source 100 for providing electrically conducting fluid to the target site. Catheter 6 generally comprises an elongate, flexible shaft body 12 including a tissue ablating region 8 at the distal end of body 12, and a proximal balloon 40 positioned on body 12 proximal to region 8. In a specific embodiment, a guide wire 28 (which may also serve as a return electrode) includes a distal balloon 18 which may be axially translated relative to region 8 and proximal balloon 40, as discussed in further detail below.

The proximal portion of catheter 6 includes a multi-lumen fitment 114 which provides for interconnections between lumens and electrical leads within catheter 6 and conduits and cables proximal to fitment 114. By way of example, a catheter electrical connector 96 is removably connected to a distal cable connector 94 which, in turn, is removably connectable to generator 80 through connector 92. One or more electrically conducting lead wires (not shown) within catheter 6 extend between one or more active electrodes at tissue ablating region 8 and one or more corresponding electrical terminals (also not shown) in catheter connector 96 via active electrode cable branch 87. In the illustrative embodiment, hollow guide wire 28 functions as the return electrode, and is electrically attached within a contact housing 111 by a sliding electrical contact (not shown). A return electrode cable branch 89 couples the sliding electrical contact to catheter connector 96. Electrical leads within cable 86 allow connection between terminals corresponding to return electrode 28 and one or more active electrodes 32 in distal cable connector 94 and generator 80.

Generator 80 is a high frequency generator operating at a frequency in the range of about 5 kHz to 20 MHZ, more preferably in the range of 30 kHz to 2.5 MHZ. The output voltage of generator 80 can be selectively applied between the return electrode and one or more active electrodes using footpedal 88, which is coupled to generator 80 via a footpedal cable 90 and removable connector 91. Generator has a selector 84 to change the applied voltage level, and may also include a second pedal (not shown) for remotely adjusting the energy level applied to the electrodes. A more complete description of a suitable generator is described in commonly assigned co-pending patent application Ser. No. 08/561,958, filed Nov. 22, 1995, the complete disclosure of which has previously been incorporated herein by reference.

Conductive fluid 30 is provided to tissue ablation region 8 of catheter 6 via a lumen (not shown in FIG. 1) within catheter 6. Fluid is supplied to lumen from the source along a conductive fluid supply line 102 and a conduit 103, which is coupled to the inner catheter lumen at multi-lumen fitment 114. The source of conductive fluid (e.g., isotonic saline) may be an irrigant pump system (not shown) or a simple gravity-driven supply, such as an irrigant reservoir 100 positioned several feet above the level of the patient and tissue ablating region 8. A control valve 104 may be positioned at the interface of fluid supply line 102 and conduit 103 to allow manual control of the flow rate of electrically conductive fluid 30. Alternatively, a metering pump or flow regulator may be used to precisely control the flow rate of the conductive fluid.

System 2 further includes an aspiration or vacuum system (not shown) to aspirate liquids and gases from the target site, and syringes 106, 108 for inflating distal and proximal balloons 18, 40, respectively. By way of example, as the plunger of syringe 108 is depressed, fluid in the syringe chamber is displaced such that it flows through a conduit 107 and an internal lumen 57 within catheter 6 (not shown in FIG. 1) to expand and inflate balloon 40. Likewise, syringe 106 is provided at the proximal end of guide wire 28 for inflating distal balloon 18, as shown by translation vectors 116, 118. Also, guidewire 28 can be advanced or retracted relative to tissue ablation region 8 of catheter 6 as shown by translation vectors 116, 118 such that, for each increment of relative displacement 116 at the proximal end of catheter 6, there is a corresponding displacement 118 of the hollow guidewire 28 relative to the tissue ablating region 8 of catheter 6.

Figure 2A:
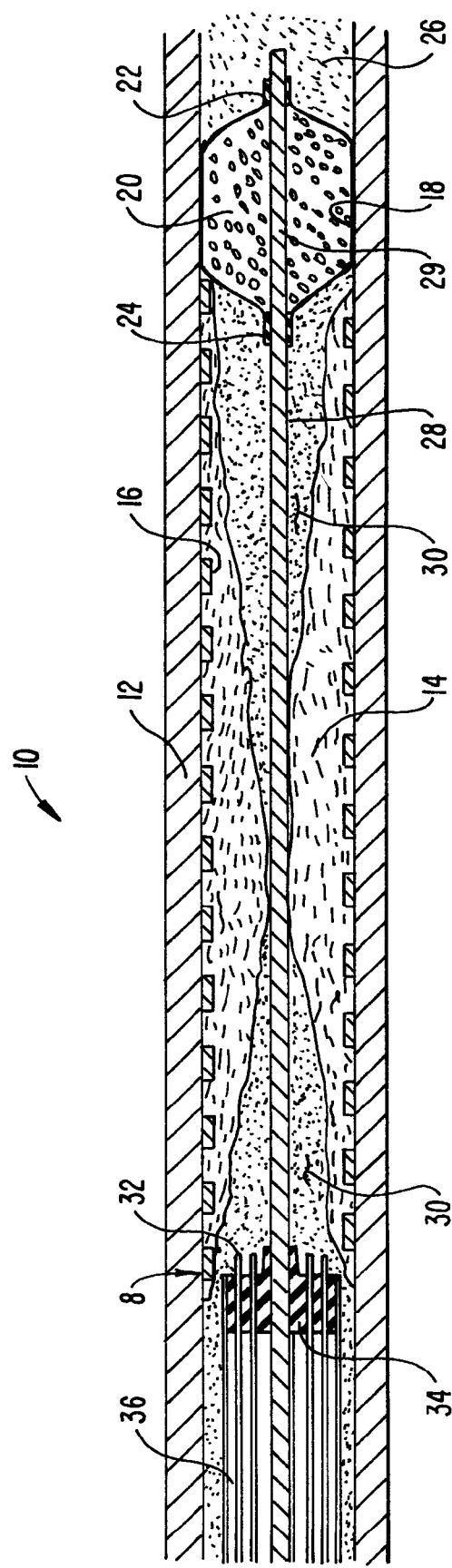
FIGS. 2A-2C illustrate a method of recanalizing an obstructed lumen according to the present invention.
Figure 2B:
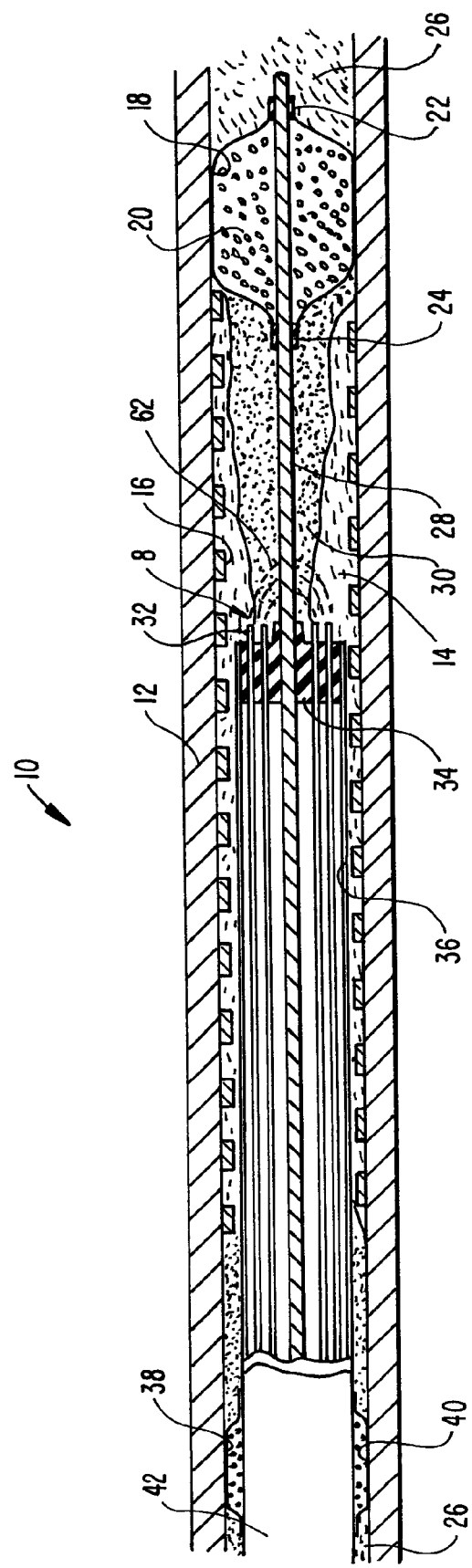
Figure 2C:
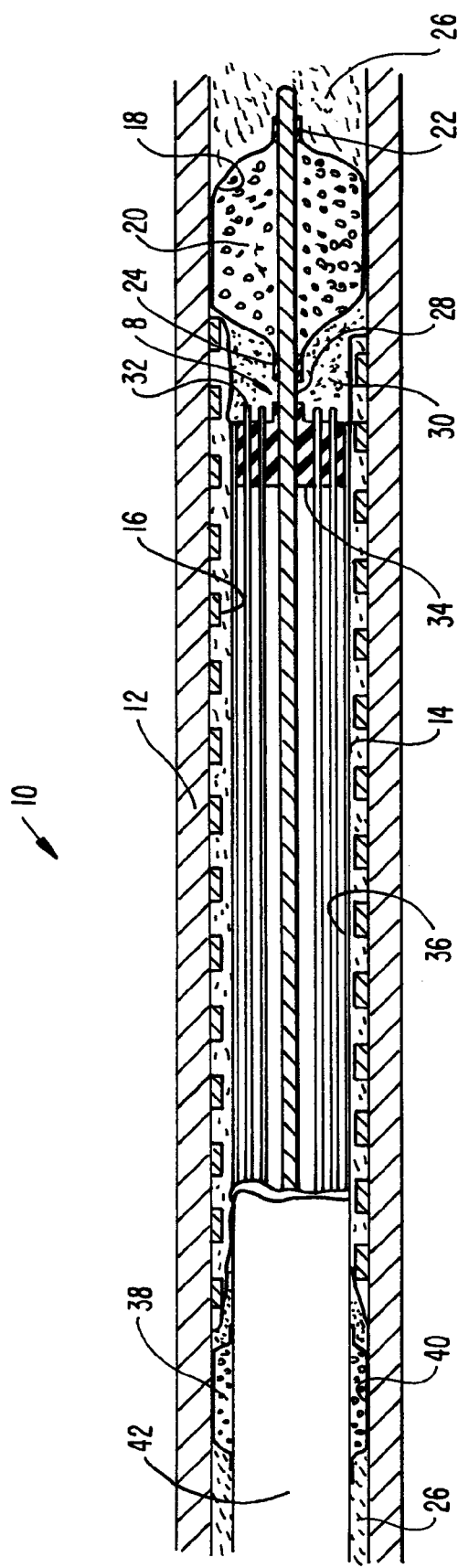

Referring now to FIGS. 2A-2C, one embodiment of the method and apparatus of the present invention will be described in detail. As shown, tissue ablation region 8 of catheter 6 progresses through occlusive media 14, such as atheromatous media or thrombus within a body passage or lumen 10, e.g., a blood vessel. The principles of the present invention are also applicable to any body lumen which becomes partially or totally occluded. The present invention is particularly useful in a lumen containing a luminal prosthesis, such as a stent 16, stent-graft, or graft, which may be metallic, non-metallic, or a metallic structure coated with a non-metallic material. A particular advantage of the present invention is the confinement of current flow paths (not shown) between the return electrode (hollow guidewire 28 in the present example) and one or more active electrodes 32 in the vicinity of tissue ablation region 8. This confinement of current flow paths minimizes the undesired flow of current through portions or all of stent 16, which may otherwise induce non-specific tissue injury beyond the site of recanalization of the occluded body lumen 10.

Referring to FIG. 2A, tissue ablating region 8 of catheter 6 is positioned proximal to the occlusive media 14 within lumen 10. The distal region of hollow guide wire 28 is positioned distal to the occlusive media 14 either before or after the initial positioning of tissue ablation region 8. Once hollow guide wire 28 is positioned as shown in FIG. 2A, proximal balloon 40 (not shown in FIG. 2A) is inflated to effect a seal between catheter shaft 42 and interior wall 12 of lumen 10 to minimize the flow of bodily fluid 26 (e.g., blood) from regions proximal to the tissue ablating region 8 of catheter 6. Electrically conductive and biologically compatible fluid 30 (e.g., isotonic saline) is delivered into lumen 10 for a sufficient period of time to displace naturally occurring bodily fluid 26 in the region between the tissue ablating region and the distal tip of guide wire 28. After the bodily fluid has been displaced, distal balloon 18 is inflated to effect a seal between balloon 18 and the interior wall 12 of lumen 10.

Once the target site is isolated from the rest of the vasculature, the supply of electrically conductive fluid 30 is continuously delivered to region 8 and balanced with the aspiration of fluid from the site of intended recanalization. The active electrode(s) 32 is (are) then energized by applying a high frequency voltage between active electrode(s) 32 and return electrode or guide wire 28. A high electric field is created at the surface of active electrode(s) 32 which causes the volumetric removal or ablation or target tissue in close proximity with active electrode(s) 32. The flow of electrical current between return electrode 28 and active electrode(s) 32 is shown by current flux lines 62 in FIG. 2B. As the occlusive media 14 is ablated, gaseous products are generated (not shown) which are entrained in the electrically conducting fluid 30 and removed through aspiration lumen 58 (not shown). The current flux lines 62 are generally confined to the central portion of tissue ablation region 8 because they generally flow inward towards return electrode 28 and because the occlusive media 14 generally shields the outer region of lumen (including stent 16) from flux lines 62. This minimizes undesirable interaction between the electrical current and stent 16.

Referring to FIG. 2C, this ablation procedure is continued until the desired length of the lumen containing occlusive media is recanalized. During the recanalization process, the products of ablation are confined between proximal balloon 40 and distal balloon 18 to minimize, for example, the injection of any non-condensible gaseous products of ablation into the blood stream which could otherwise lead to the formation of injurious or life-threatening emboli. Once the occlusive media 14 has been volumetrically removed (i.e., ablated), the energy application is suspended, the valve on the aspiration lumen is closed, control valve 104 is closed and balloons 18, 40 are deflated. The time period from the initial inflation of balloons 18, 40 to the deflation of these balloons is typically about 15-45 seconds, depending on the length and the extent of occlusion in the vessel. For longer occlusions, the above process may be repeated several times with intervals of no balloon inflation so that vital oxygen-bearing blood can be reperfused through the zone of intended recanalization to preserve the tissue distal to the recanalization zone.

Figure 3A:
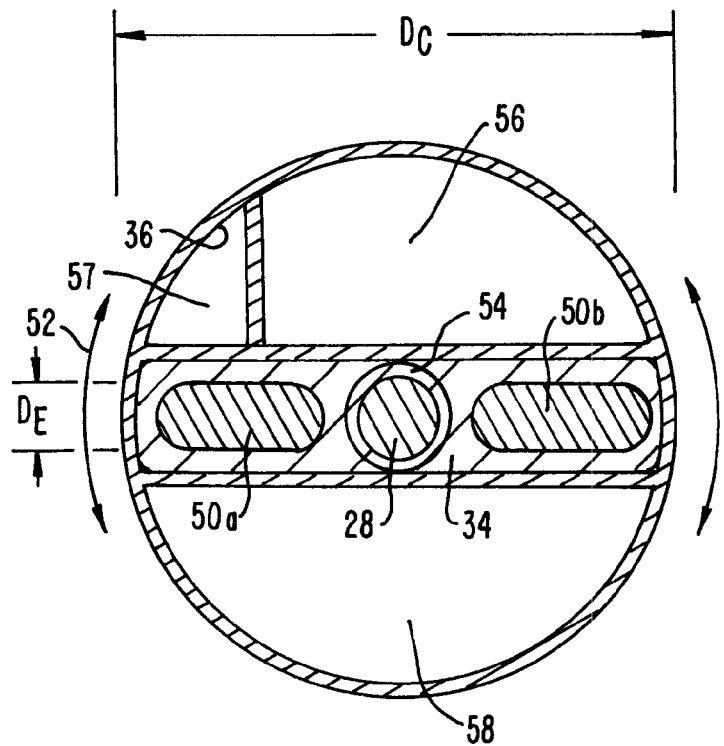
FIGS. 3A and 3B are transverse and longitudinal cross-sectional views, respectively, of a first embodiment of the distal portion of the catheter.
Figure 3B:
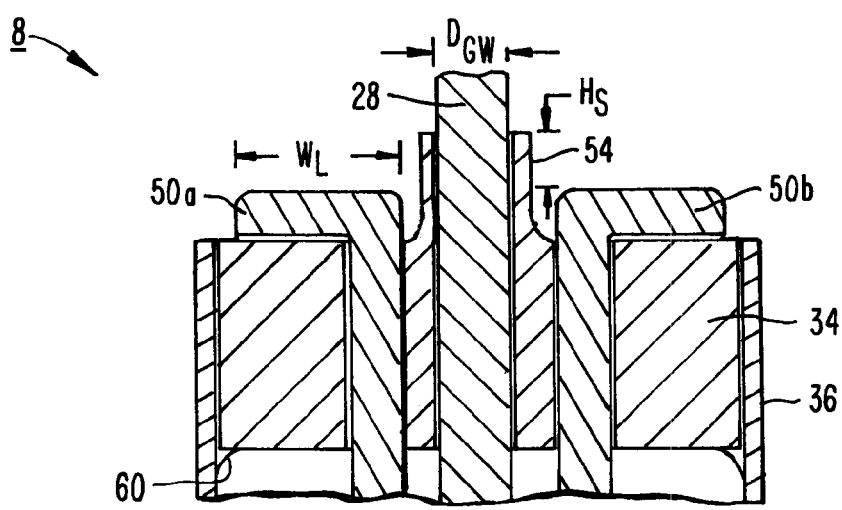

A first embodiment of tissue ablation region 8 of catheter 6 is shown in FIGS. 3A and 3B. As shown, two active electrodes 50a and 50b are secured within an electrically insulating support member 34. The electrodes 50a, 50b are preferably composed of a refractory, electrically conductive metal or alloy, such as platinum, titanium, tantalum, tungsten, stainless steel and the like. The support member 34 is secured to the distal end of catheter 6 with a biocompatible adhesive 60 between support member 34 and outer sleeve 36. An inorganic electrically insulating sleeve 54 preferably extends above the distal plane of active electrodes 50a, 50b by a distance $H_s$. A central lumen in support member 34 provides a passageway for guide wire 28 that permits axial displacement and rotation of tissue ablating region 8 relative to guide wire 28.

In an exemplary embodiment, the support member 34 will comprise an inorganic insulator, such as ceramic, glass, glass/ceramic or a high resistivity material, such as silicon or the like. An inorganic material is generally preferred for the construction of the support member 34 since organic or silicone based polymers are known to rapidly erode during sustained periods of the application of high voltages between electrodes 50 and the return electrode 28 during tissue ablation. However, for situations in which the total cumulative time of applied power is less than about one minute, organic or silicone based polymers may be used without significant erosion and loss of material of the support member 34 and, therefore, without significant reduction in ablation performance.

As shown in FIG. 3A, an irrigation lumen 56 and an aspiration lumen 58 are provided to inject electrically conducting fluid 30 and remove gaseous products of ablation 48 from the site of recanalization. An additional fluid lumen 57 provides fluid communication between inflation syringe 108 and proximal balloon 40. This fluid lumen 57 is filled with a sealant in those portions of the catheter distal to proximal balloon 40.

In use with the present invention, catheter 6 is rotated about 180 degrees clockwise and then about 180 degrees counter clockwise as the electrodes 50 are energized by generator 80 (FIG. 1) to effect ablation of the occlusive media. Using a reciprocating rotational motion combined with a small pressure to advance tissue ablation region 8 through the longitudinal length of the occlusive media 14 allow recanalization of the occluded vessel as described with reference to FIGS. 2A-2C. The cross-sectional shape of the active electrodes may be round wires as shown in FIG. 3B, or they may have shaped surfaces to enhance the electric field intensity at the distal surfaces of the active electrodes 50. Suitable electrode designs for use with the present invention may be found in co-pending, commonly assigned application Ser. No. 08/687,792, filed Jul. 19, 1996, the complete disclosure of which is incorporated herein by reference for all purposes.

Return electrode 28 comprises an electrically conducting material, usually metal, which is selected from the group consisting of stainless steel alloys, platinum or its alloys, titanium or its alloys, molybdenum or its alloys, and nickel or its alloys. The return electrode 28 may be composed of the same metal or alloy which forms the active electrodes 50 to minimize any potential for corrosion or the generation of electrochemical potentials due to the presence of dissimilar metals contained within an electrically conductive fluid 30, such as isotonic saline (discussed in greater detail below).

Figure 4A:
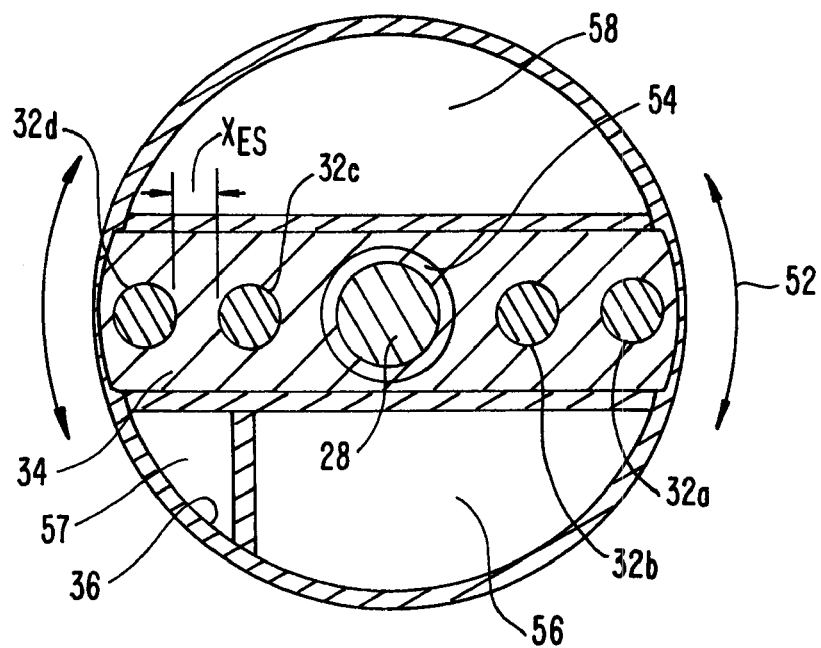
FIGS. 4A and 4B are transverse and longitudinal cross-sectional views, respectively, of a second embodiment of the distal portion of the catheter.
Figure 4B:
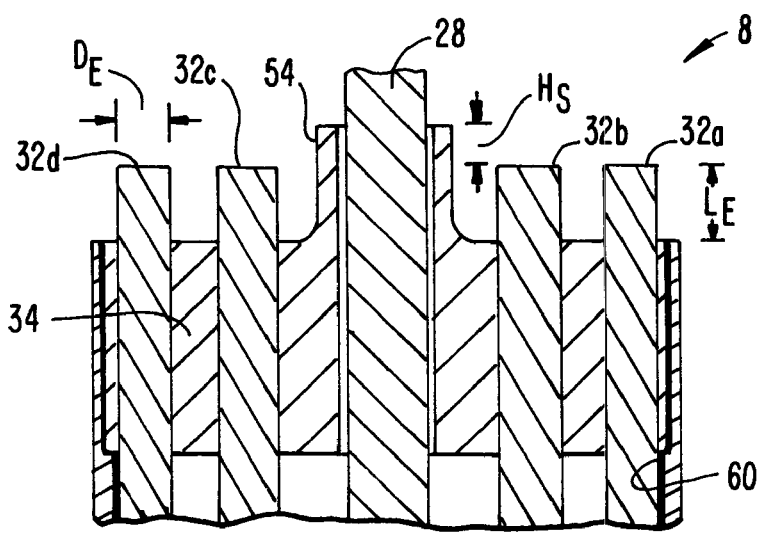

Referring now to FIGS. 4A and 4B, a second embodiment of tissue ablation region 8 of catheter 6 will now be described. In this embodiment, four active electrodes 32a, 32b, 32c, 32d are secured within an inorganic electrically insulating support member 34. Similar to the previous embodiment, support member 34 is secured to the distal end of catheter 6 with a biocompatible adhesive 60 between support member 34 and outer sleeve 36. An inorganic electrically insulating sleeve 54 preferably extends above the distal plane of active electrodes 50a, 50b by a distance $H_s$. A central lumen in support member 34 provides a passageway for guide wire 28 that permits axial displacement and rotation of tissue ablating region 8 relative to guide wire 28. As shown in FIG. 4A, an irrigation lumen 56 and an aspiration lumen 58 are provided to inject electrically conducting fluid 30 and remove gaseous products of ablation 48 from the site of recanalization. An additional fluid lumen 57 provides fluid communication between inflation syringe 108 and proximal balloon 40. This fluid lumen 57 is filled with a sealant in those portions of the catheter distal to proximal balloon 40.

In use, catheter 6 is rotated about 180 degrees clockwise and then about 180 degrees counter clockwise as the electrodes 32 are energized by generator 80 (FIG. 1) to effect ablation of the occlusive media. Using a reciprocating rotational motion combined with a small pressure to advance tissue ablation region 8 through the longitudinal length of the occlusive media 14 allow recanalization of the occluded vessel as described with reference to FIGS. 2A-2C. The cross-sectional shape of the active electrodes may be round wires as shown in FIG. 4B, or they may have shaped surfaces to enhance the electric field intensity at the distal surfaces of the active electrodes 32 as described co-pending, commonly assigned application Ser. No. 08/687,792, filed Jul. 19, 1996, the complete disclosure of which has previously been incorporated herein by reference.

Figure 5A:
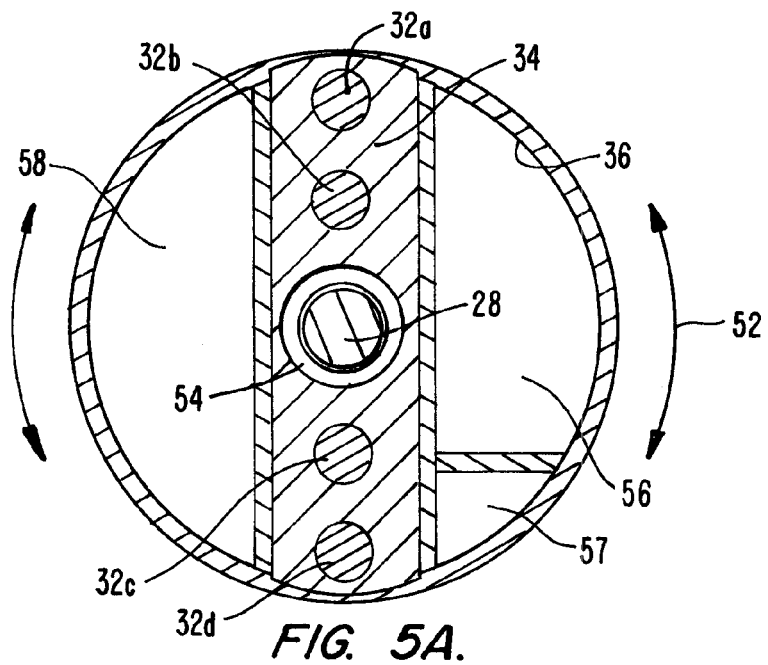
FIGS. 5A and 5B are transverse and longitudinal cross-sectional views, respectively, of the second embodiment of the distal portion of the catheter further illustrating the inflow of conductive liquid and aspiration of conductive liquid and gaseous products.
Figure 5B:
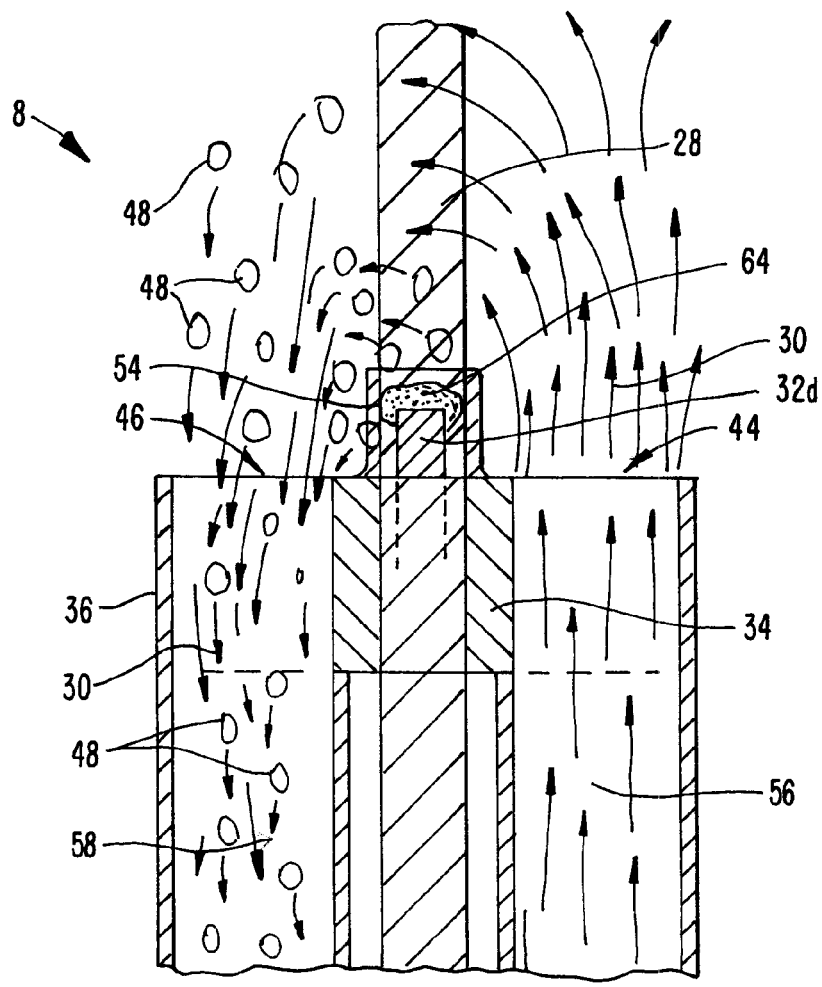

The second embodiment of FIGS. 4A and 4B is illustrated in greater detail in FIGS. 5A and 5B. As shown, electrically conductive fluid flows through irrigation lumen 56 of catheter 6 to and through irrigation port 44 and subsequently surrounds the target tissue site (i.e., occlusive media 14). When high-frequency voltage is applied between the return electrode 28 and active electrodes 32, a vapor layer 64 forms at and around active electrodes 32 with concomitant volumetric removal (ablation) of the occlusive media 14. A more detailed description of this phenomena can be found in commonly assigned, co-pending application Ser. No. 08/561,958, filed on Nov. 22, 1995, the complete disclosure of which has previously been incorporated herein by reference. The occlusive media 14 is decomposes into gaseous products of ablation 48 which are entrained in electrically conducting fluid 30 and evacuated through aspiration port 46 and to the proximal end of catheter 6 via aspiration lumen 58.

Figure 6A:
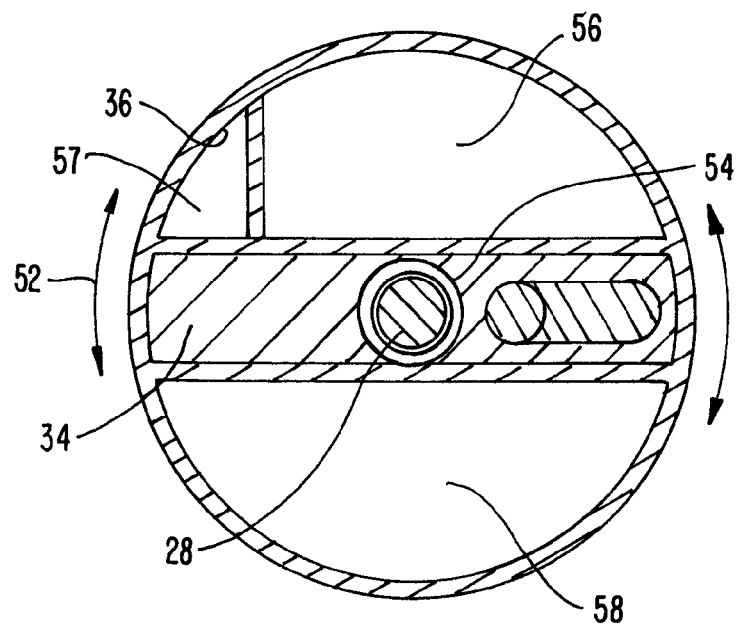
FIGS. 6A and 6B are transverse and longitudinal cross-sectional views, respectively, of a third embodiment of the distal portion of the catheter.
Figure 6B:
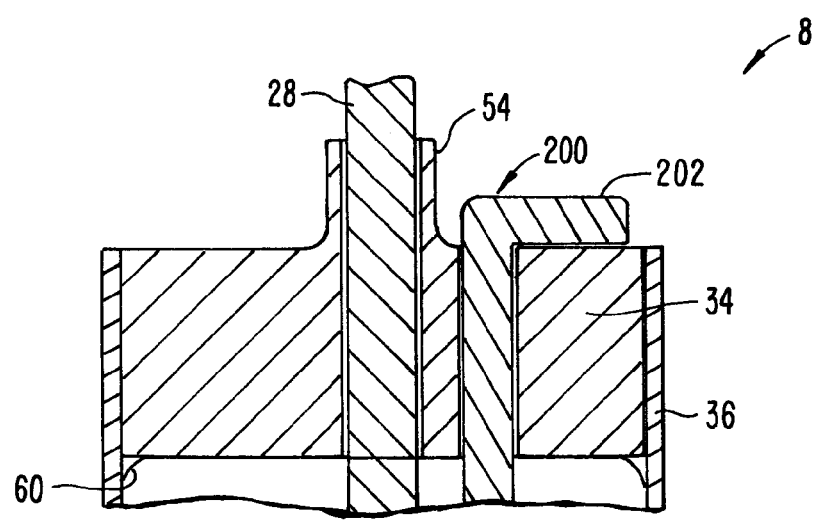

A third embodiment of tissue ablation region 8 is illustrated in FIGS. 6A and 6B. Many of the elements of this embodiment are the same as previous embodiments, and therefore will not be repeated. As shown, a single active electrode 200 is secured within support member 34. Active electrode 200 preferably has an L-shaped distal end so that a distal portion 202 of electrode 200 extends radially outward along the distal surface of support member 34. As before, electrode 200 is rotated in both directions, as the region 8 is advanced through the lumen to recanalize the lumen.

Figure 7A:
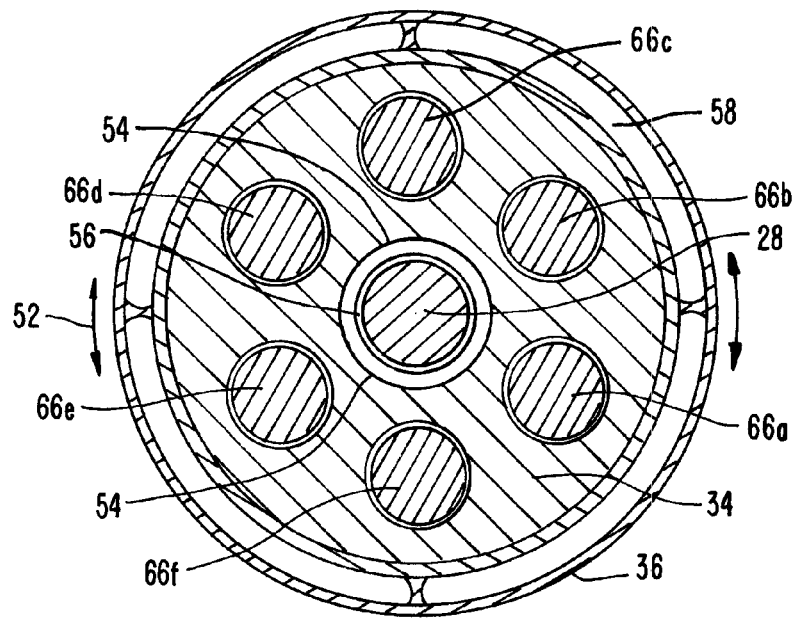
FIGS. 7A and 7B are transverse and longitudinal cross-sectional views, respectively, of a fourth embodiment of the distal portion of the catheter.
Figure 7B:
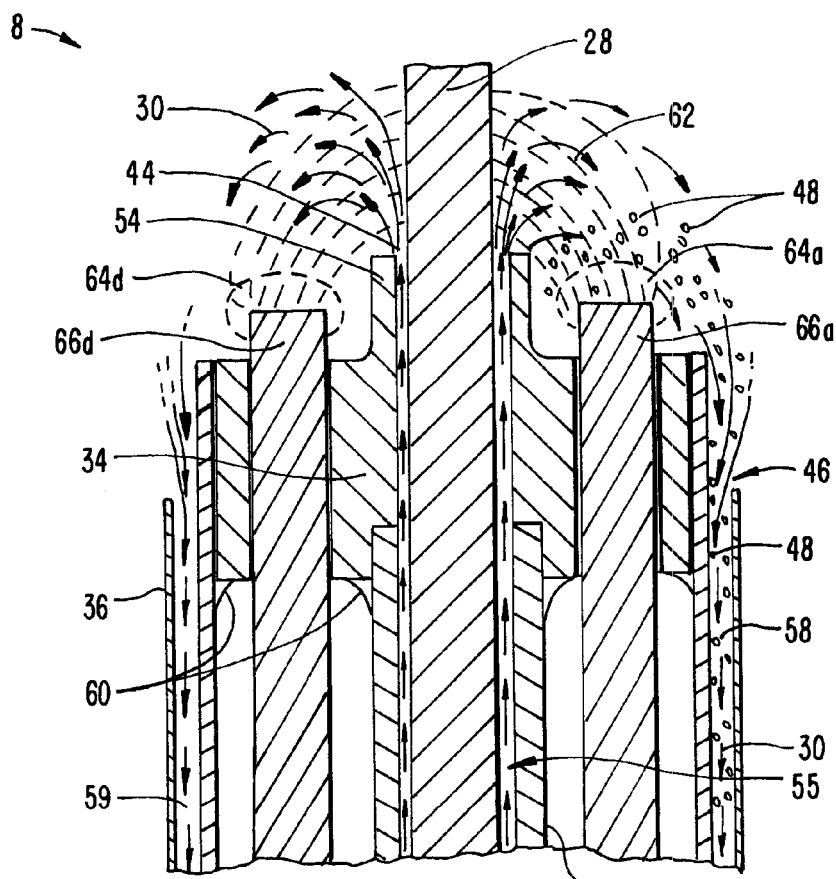

A fourth embodiment of tissue ablation region 8 is illustrated in FIGS. 7A and 7B. Many of the elements of this embodiment are the same as previous embodiments, and therefore will not be repeated. As shown, six active electrodes 66a-66f are secured within inorganic support member 34. An annular irrigation lumen 55 and an aspiration lumen 59 are provided to inject electrically conducting fluid 30 and remove gaseous products of ablation 48 from the site of recanalization. When high frequency voltage is applied between the return electrode 28 and active electrodes 66, a vapor layer 64 forms at and around active electrodes 66 with concomitant volumetric removal (ablation) of the occlusive media 14. For this embodiment and that shown in FIGS. 8A and 8B, rotation may be limited to +−30 degrees due to the greater number and circumferential distribution of active electrodes. The power or current supplied to each electrode may be individually controlled by active or passive mechanisms as previously described in commonly assigned, co-pending application Ser. No. 08/561,958, filed on Nov. 22, 1995. The occlusive media 14 is decomposed into gaseous products of ablation 48 which are entrained in electrically conducting fluid 30 and evacuated through aspiration port 46 and onto the proximal end of catheter 6 via aspiration lumen 59. As shown in FIG. 7b, the current flux lines 62 are confined to the central portions of tissue ablation region 8.

Figure 8A:
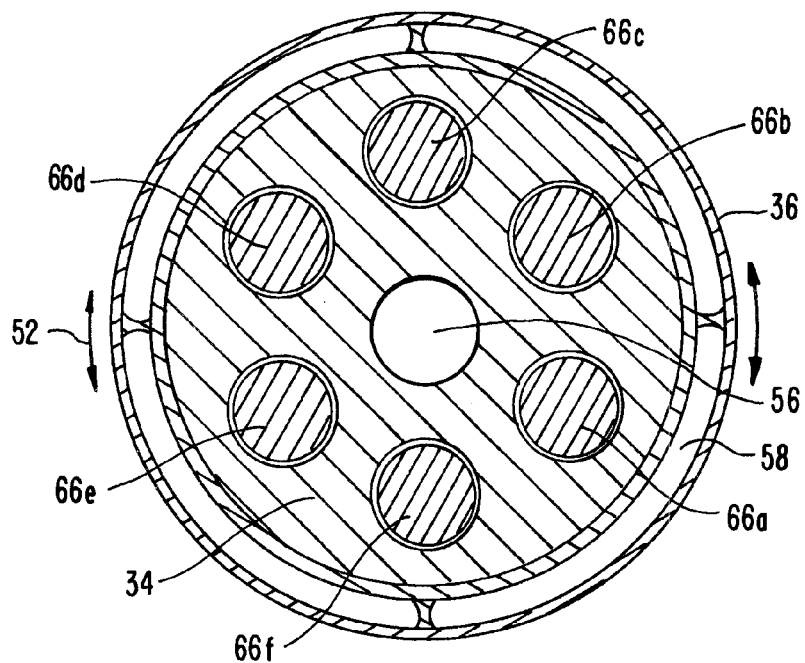
FIGS. 8A and 8B are transverse and longitudinal cross-sectional views, respectively, of a fifth embodiment of the distal portion of the catheter.
Figure 8B:
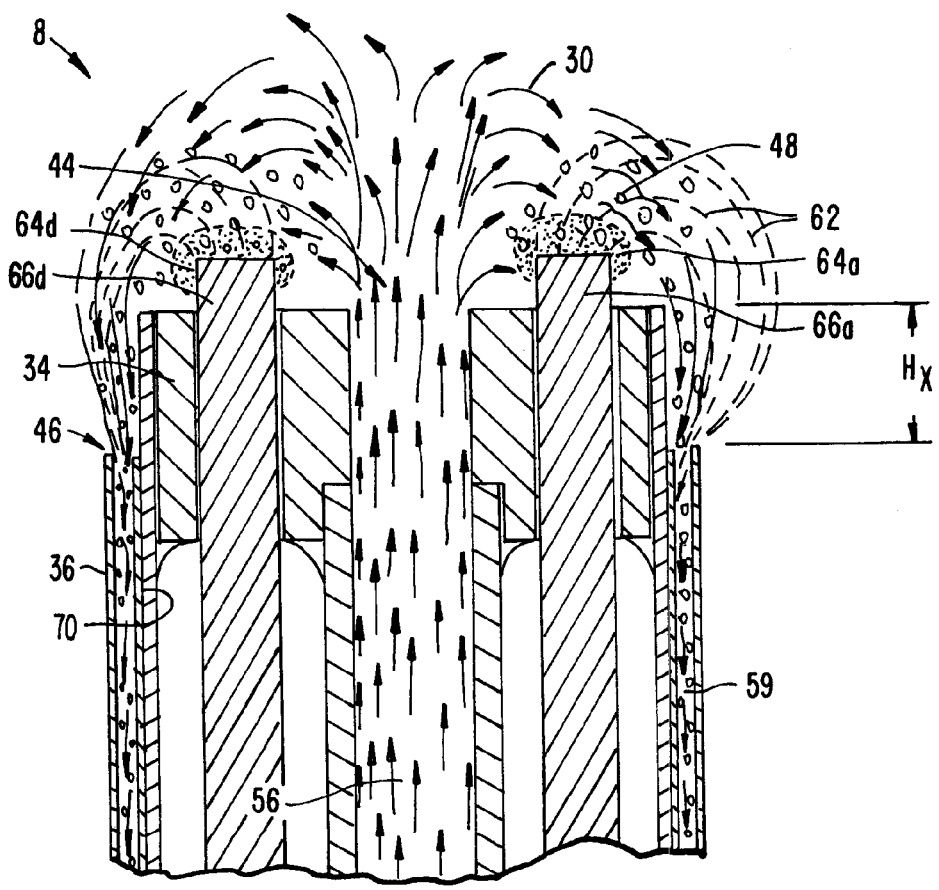

FIGS. 8A and 8B illustrate a fifth embodiment of the present invention. This embodiment is similar to the fourth embodiment in that six active electrodes 66a-66f are secured within inorganic support member 34. A return electrode 70 (e.g., metal sleeve) is positioned proximal to the active electrodes 66a-66f by a distance $H_x$. In this embodiment, current flux lines 62 travel proximally from the distal tips of electrodes 66 to the proximally spaced return electrode 70.

Figure 9A:
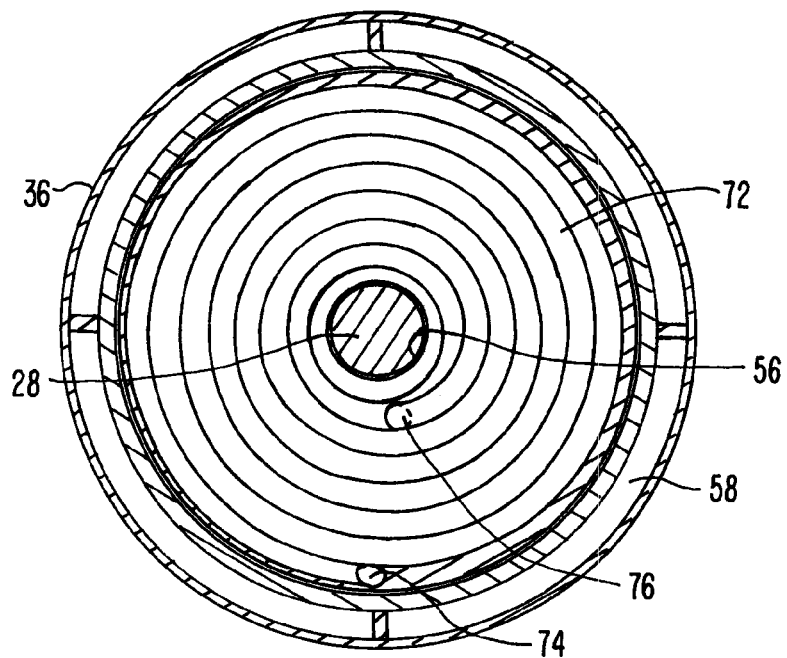
FIGS. 9A and 9B are transverse and longitudinal cross-sectional views, respectively, of a sixth embodiment of the distal portion of the catheter.
Figure 9B:
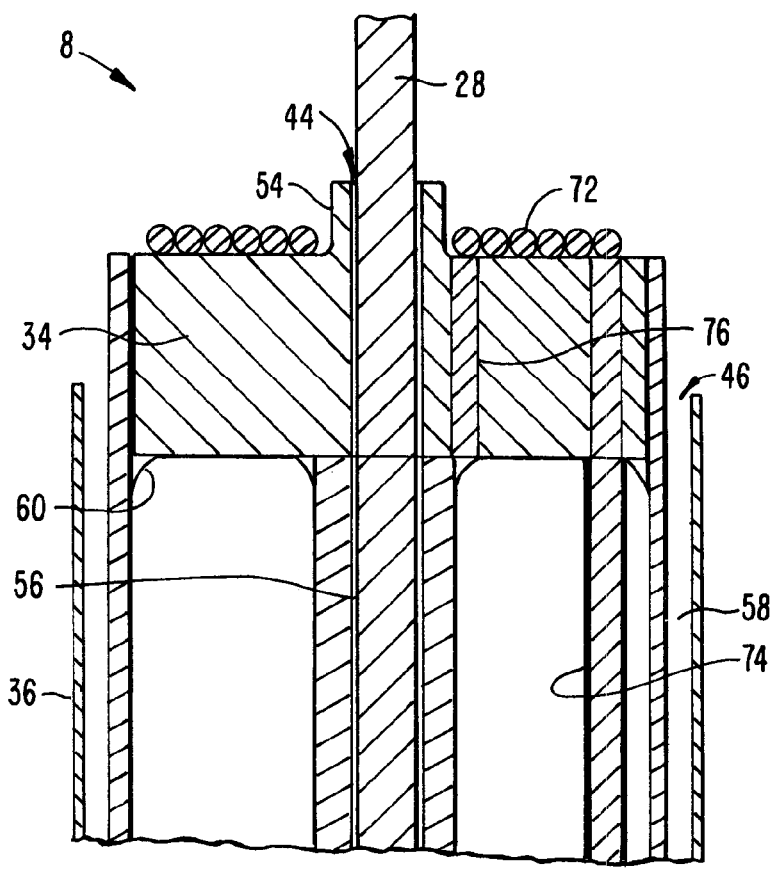

Referring to FIGS. 9A and 9B, a sixth embodiment of the invention will now be described. As shown, a single active electrode 72 is secured within inorganic support member 34. In this embodiment, active electrode 72 comprises a coiled wire having a plurality of concentric coils tightly and helically wrapped and secured on support member 34 (FIG. 9B). Preferably, the helical coil extends around return electrode 28 in concentric configuration, as shown in FIG. 9A.

Figure 10A:
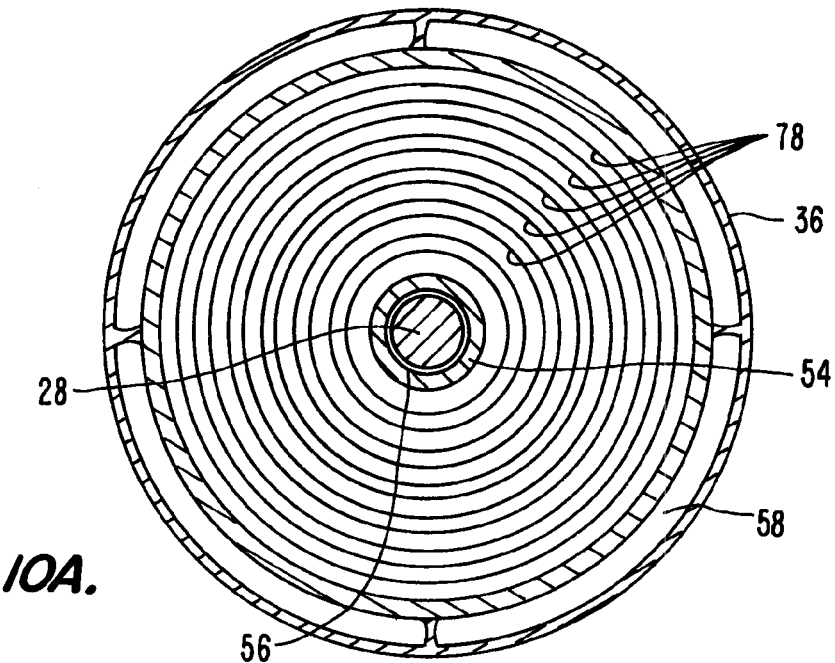
FIGS. 10A and 10B are transverse and longitudinal cross-sectional views, respectively, of a seventh embodiment of the distal portion of the catheter.
Figure 10B:
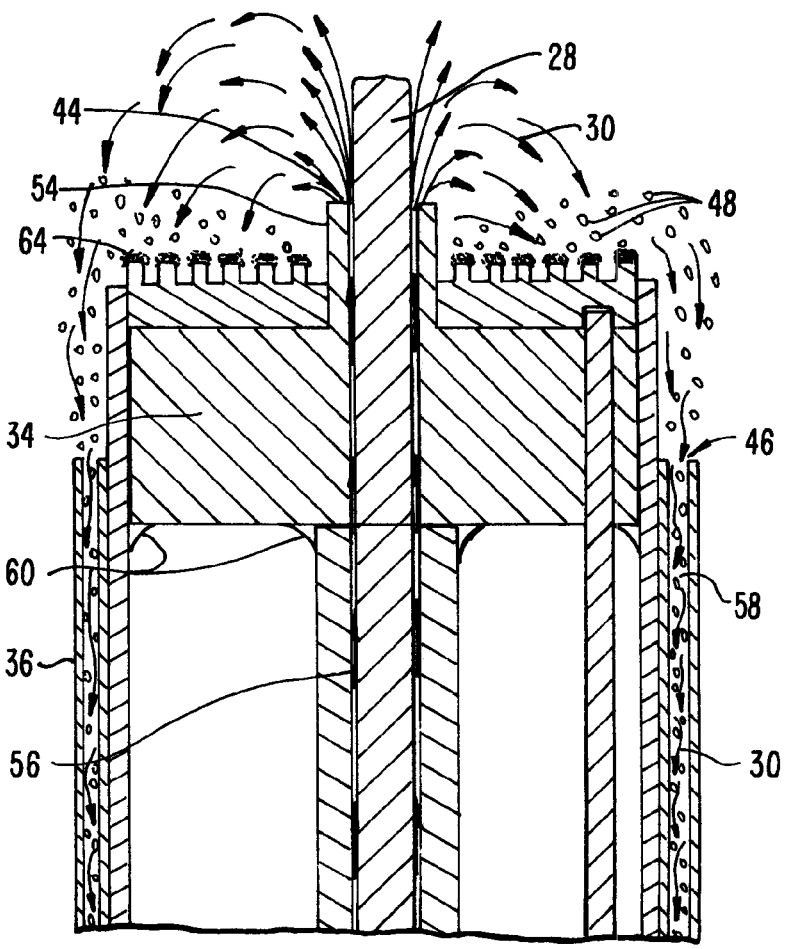

A seventh embodiment of the invention is shown in FIGS. 10A and 10B. This embodiment is similar to the sixth embodiment except that the single active electrode 73 defines a series of concentric machined grooves 75 to form concentric circular electrodes 78 surrounding return electrode 28. The distal edges of electrodes 78 generate regions of high electric field intensities when high frequency voltage is applied between return electrode 28 and concentric active electrodes 78. A vapor layer 64 forms at and around active electrodes 78 with concomitant volumetric removal (ablation) of the occlusive media. The embodiments of FIGS. 9 and 10 are usually advanced through the occlusive media without rotation.

What is claimed is:

1. A catheter system for maintaining patency in a body passage having an intraluminal prosthesis positioned therein, the prosthesis having a cylindrical wall, wherein occlusive media has grown through or around the cylindrical wall of the prosthesis and into the body passage, the catheter system comprising:

a catheter body having a distal end portion and a proximal end portion, the distal end portion being sized to pass through the prosthesis;

at least one active electrode positioned on the distal end portion of the catheter body;

a return electrode positioned on the distal end portion of the catheter body; and at least one connector extending through the catheter body for electrically coupling the at least one active electrode and the return electrode to a source of high frequency electrical energy;

wherein said at least one active electrode and said return electrode are sized and positioned such that electrically conductive fluid in a pathway between said electrodes forms a plasma when selected voltage potentials are applied to said electrodes from said source of high frequency electrical energy, and wherein said occlusive media is disintegrated by said plasma wherein said at least one active electrode and said return electrode are configured such that current flow through the prosthesis is minimized and wherein the catheter system further comprises an electrically insulating support member affixed to the distal end portion of the catheter body, the at least one active electrode being secured within the support member, and the support member comprising an inorganic material and wherein the support member has a central lumen therethrough, and wherein the catheter system further comprises a guidewire disposed within the central lumen, wherein the catheter body is axially and rotationally moveable with respect to the guidewire.

2. The catheter system of claim 1, further comprising:

a source of electrically conductive fluid; and an internal lumen within the catheter body, the internal lumen coupled to the source of electrically conductive fluid for delivering the electrically conductive fluid between the return electrode and the at least one active electrode.

3. The catheter system of claim 1, further comprising an aspiration system for aspirating products of ablation from the body passage in a region around the occlusive media.

4. The catheter system of claim 3, wherein the aspiration system comprises:
- a suction lumen within the catheter body, the suction lumen having a distal opening adjacent to the at least one active electrode; and
- a vacuum system coupled to the suction lumen.

5. The catheter system of claim 1, further comprising a fluid delivery system for displacing naturally occurring body fluids from the body passage in a region around the occlusive media.

6. The catheter system of claim 5, wherein the fluid delivery system comprises:
- a source of electrically conductive fluid; and
- an internal lumen within the catheter body, the internal lumen coupled to the electrically conductive fluid source for delivering the electrically conductive fluid to the distal end portion of the catheter body.

7. The catheter system of claim 1, wherein the at least one active electrode comprises at least six, electrically independent, active electrodes, each of the six active electrodes extending distally from said electrically insulating support member disposed at the distal end portion of the catheter body.

8. The catheter system of claim 1, further comprising a power limiting element coupled to the at least one active electrode for limiting power to the at least one active electrode based on impedance between the at least one active electrode and the return electrode.

9. The catheter system of claim 1, wherein the at least one active electrode and the return electrode jointly define a tissue ablation region of the catheter system, wherein the current flow path is substantially confined to the tissue ablation region, thereby preventing electric current flow to the prosthesis, and preventing injury to the body passage.

10. The catheter system of claim 1, wherein the at least one active electrode is a plurality of active electrodes that are substantially cylindrical.

11. The catheter system of claim 10, wherein each of the plurality of active electrodes comprises a material selected from the group consisting of: platinum, stainless steel, titanium, tantalum, tungsten, and their alloys.

12. The catheter system of claim 10, wherein the plurality of active electrodes comprise six active electrodes.

13. The catheter system of claim 12, wherein the six active electrodes are distributed in a circular arrangement within said support member.

14. The catheter system of claim 10, wherein the plurality of active electrodes are electrically independent from each other.

15. The catheter system of claim 1, further comprising said high frequency electrical energy source.

16. The catheter of claim 1, wherein the return electrode is associated with a guidewire that is axially movable relative to said active electrode.

17. The catheter of claim 1, wherein the prosthesis is a stent adapted to maintain the patency of blood vessels.

18. The catheter of claim 16, further comprising an inflatable member positioned distal to said active electrode, said inflatable member being inflatable to occlude the lumen downstream of the active electrode such that fragments of tissue are prevented from moving distal of said inflatable member.

19. A catheter system for maintaining patency in a body passage having an intraluminal prosthesis positioned therein, the prosthesis having a cylindrical wall, wherein occlusive media has grown through or around the cylindrical wall of the prosthesis and into the body passage, the catheter system comprising:
- a catheter body having a distal end portion and a proximal end portion, the distal end portion being sized to pass through the prosthesis, said catheter body comprising a guidewire lumen;
- at least one active electrode positioned on the distal end portion of the catheter body;
- a return electrode positioned on the distal end portion of the catheter body; and
- at least one connector extending through the catheter body for electrically coupling the at least one active electrode and the return electrode to a source of high frequency electrical energy;
- wherein said at least one active electrode and said return electrode are adapted such that electrically conductive fluid in a pathway between said electrodes forms a plasma when selected voltage potentials are applied to said electrodes from said source of high frequency electrical energy, and wherein said occlusive media is disintegrated by said plasma and wherein the catheter system further comprises a guidewire disposed within the guidewire lumen, wherein the catheter body is axially and rotationally moveable with respect to the guidewire.

20. A catheter system for maintaining patency in a body passage having an intraluminal prosthesis positioned therein, the prosthesis having a cylindrical wall, wherein occlusive media has grown through or around the cylindrical wall of the prosthesis and into the body passage, the catheter system comprising:
- a catheter body having a distal end portion and a proximal end portion, the distal end portion being sized to pass through the prosthesis, said catheter body comprising a guidewire lumen;
- at least one active electrode positioned on the distal end portion of the catheter body;
- a return electrode positioned on the distal end portion of the catheter body;
- at least one connector extending through the catheter body for electrically coupling the at least one active electrode and the return electrode to a source of high frequency electrical energy wherein said at least one active electrode and said return electrode are adapted such that electrically conductive fluid in a pathway between said electrodes forms an electrically conductive pathway when a voltage potential is applied between said electrodes from said source of high frequency electrical energy such that said occlusive media is removed; and
- a guidewire disposed within the guidewire lumen such that said catheter is axially and rotationally moveable with respect to the guidewire.

* * * * *